US009952157B2

(12) United States Patent
Utzinger et al.

(10) Patent No.: US 9,952,157 B2
(45) Date of Patent: Apr. 24, 2018

(54) TISSUE IMAGING AND VISUALIZATION OF LESIONS USING REFLECTANCE AND AUTOFLUORESCENCE MEASUREMENTS

(71) Applicant: The Arizona Board of Regents on behalf of the University of Arizona, Tucson, AZ (US)

(72) Inventors: Urs Utzinger, Tucson, AZ (US); Bhaskar Banerjee, Tucson, AZ (US); Timothy E. Renkoski, Tucson, AZ (US); Nathaniel S. Rial, Tucson, AZ (US); Logan Graves, Tucson, AZ (US)

(73) Assignee: The Arizona Board of Regents on behalf of the University of Arizona, Tucson, AZ (US)

(*) Notice: Subject to any disclaimer, the term of this patent is extended or adjusted under 35 U.S.C. 154(b) by 212 days.

(21) Appl. No.: 14/415,311

(22) PCT Filed: Jul. 16, 2013

(86) PCT No.: PCT/US2013/050753
§ 371 (c)(1),
(2) Date: Jan. 16, 2015

(87) PCT Pub. No.: WO2014/014956
PCT Pub. Date: Jan. 23, 2014

(65) Prior Publication Data
US 2015/0185151 A1 Jul. 2, 2015

Related U.S. Application Data

(60) Provisional application No. 61/849,610, filed on Jan. 30, 2013, provisional application No. 61/741,310, filed on Jul. 17, 2012.

(51) Int. Cl.
*G01N 21/00* (2006.01)
*G01N 21/64* (2006.01)
(Continued)

(52) U.S. Cl.
CPC ..... *G01N 21/6486* (2013.01); *A61B 1/00009* (2013.01); *G01N 21/4795* (2013.01);
(Continued)

(58) Field of Classification Search
CPC ... A61B 5/0059; A61B 5/7257; A61B 5/0071; A61B 5/0075; A61B 5/1455;
(Continued)

(56) References Cited

U.S. PATENT DOCUMENTS 5,507,287 A 4/1996 Palcic et al.
5,590,660 A 1/1997 MacAulay et al.
(Continued)

FOREIGN PATENT DOCUMENTS

EP 1087698 A1 4/2001
EP 1261280 A2 12/2002
(Continued)

OTHER PUBLICATIONS

Qu et al., "Mechanisms of ratio fluorescence imaging of diseased tissue", SPIE, v. 2387, 1995, pp. 71-79.*
(Continued)

*Primary Examiner* — Yelena G Gakh
(74) *Attorney, Agent, or Firm* — Klarquist Sparkman, LLP

(57) ABSTRACT

Methods for reliable identification of low-contrast lesions within a tissue of a subject comprise delivering an excitation signal to the tissue, wherein the excitation signal is selected to stimulate tissue to produce autofluorescence and/or reflectance. The autofluorescence and/or reflectance is detected, and ratiometric images are produced based on the autofluorescence and/or reflectance images. An imaging system is provided which is configured to carry out such methods, irradiating tissue at a various possible excitation wave-
(Continued)

lengths, such as UV excitation wavelengths below 300 nm, to elicit fluorescence from specific native fluorophores.

21 Claims, 14 Drawing Sheets

(51) Int. Cl.
*A61B 1/00* (2006.01)
*G01N 21/47* (2006.01)
*G01N 21/55* (2014.01)
*G01N 33/483* (2006.01)
*A61B 1/04* (2006.01)

(52) U.S. Cl.
CPC ......... *G01N 21/55* (2013.01); *G01N 21/6456* (2013.01); *G01N 33/4833* (2013.01); *A61B 1/0005* (2013.01); *A61B 1/043* (2013.01); *G01N 21/6458* (2013.01); *G01N 2021/6484* (2013.01)

(58) Field of Classification Search
CPC ... A61B 1/043; A61B 1/00009; A61B 5/0073; A61B 5/0066; A61B 5/0261; A61B 5/7203; A61B 1/045; A61B 1/00186; A61B 1/0638

See application file for complete search history.

(56) References Cited

U.S. PATENT DOCUMENTS

| | | | |
|---|---|---|---|
| 5,769,792 | A | 6/1998 | Palcic et al. |
| 6,405,070 | B1 | 6/2002 | Banerjee |
| 6,405,074 | B1 | 6/2002 | Banerjee |
| 7,257,437 | B2 | 8/2007 | Demos et al. |
| 7,722,534 | B2 | 5/2010 | Cline |
| 7,932,502 | B2 | 4/2011 | Kubo et al. |
| 8,010,185 | B2 | 8/2011 | Ueda |
| 2003/0055341 | A1 | 3/2003 | Banerjee |
| 2004/0006276 | A1 | 1/2004 | Demos et al. |
| 2004/0038320 | A1 | 2/2004 | Banerjee |
| 2008/0051664 | A1 | 2/2008 | Demos et al. |
| 2008/0255426 | A1 | 10/2008 | Iketani |
| 2010/0254589 | A1 | 10/2010 | Gallagher |

FOREIGN PATENT DOCUMENTS

| | | |
|---|---|---|
| WO | WO 9965394 A1 | 12/1999 |
| WO | WO 0169199 A2 | 9/2001 |

OTHER PUBLICATIONS

Li and Xie, "Autofluorescence excitation-emission matrices for diagnosis of colonic cancer", World J. Gastroenterol., 2005, v. 11, No. 25, pp. 3931-3934.*

Adachi et al., Development of the Autofluorescence Endoscope Imaging System Diagnostic and Therapeutic Endoscopy, vol. 5, pp. 65-70, 1999.

Andersson et al., "Autofluorescence of living cells," *Journal of Microscopy*, vol. 191, part 1, 3 pgs., Jul. 1998.

Jacobson et al., "In vivo imaging of bladder cancer using prototype endoscope-adaptable system providing parallel RGB and NIR autofluorescence image acquisition," *Proceedings of SPIE*, vol. 8220, 2012.

Li et al., "Two-photon autofluorescence microscopy of multicolor excitation," *Optics Letters*, vol. 34, No. 2, 2 pgs., Jan. 15, 2009.

Lin et al., "Endoscope-based autofluorescence imaging and point spectroscopy for improving cancer detection in the larynx," *Asia Communications and Photonics . . .*, 2 pp., 2009 (opticsinfobase.org).

Moriyama et al., "A Ratiometric Fluorescence Imaging System for Surgical Guidance," *Advances in Optical Technologies*, 10 pgs., vol. 2008.

Nakaniwa et al., "Newly Developed Autofluorescence Imaging Videoscope System for the Detection of Colonic Neoplasms," *Digestive Endoscopy*, 17, 235-240, 2005.

Nakhosteen et al., "Autofluorescence Bronchoscopy: The Laser Imaging Fluorescence Endoscope," *Interventional Bronchoscopy*, vol. 30, pp. 236-242, 2000.

Nakhosteen, "Autofluorescence Bronchoscopy the Laser Imaging Fluorescence Endoscope (LIFE®)," *The 22nd Annual Congress of the Japan Society for Bronchology, JJSB*, 21(8): 531-534, 1999.

* cited by examiner

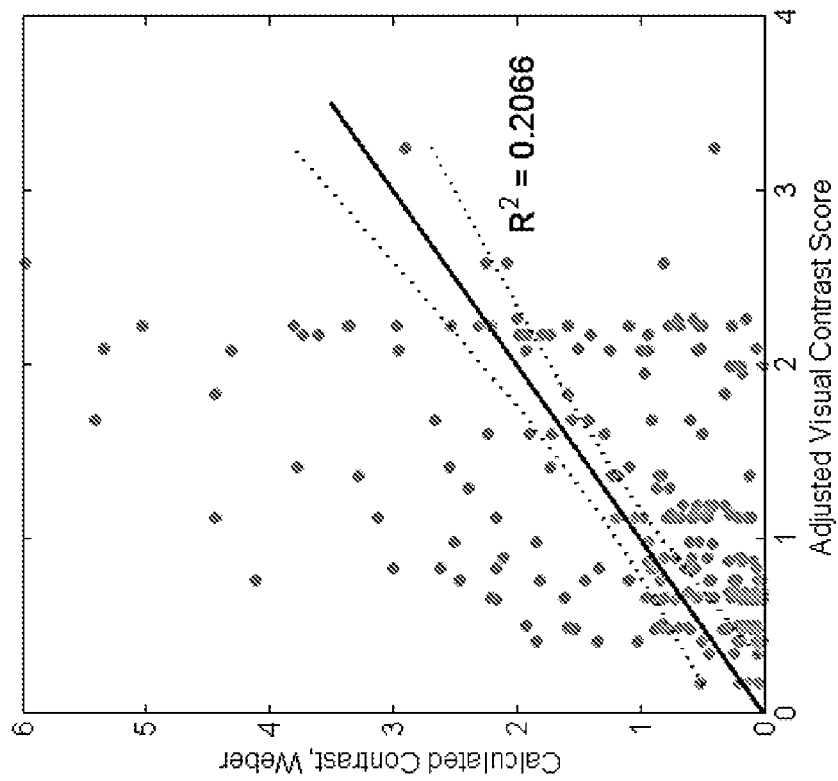
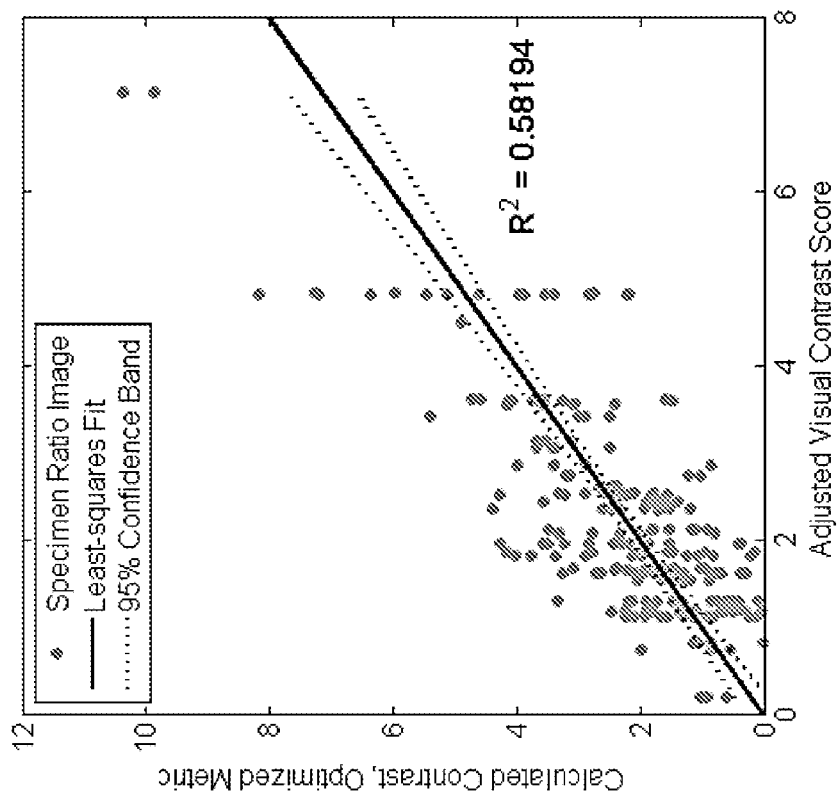
FIG. 8A
FIG. 8B

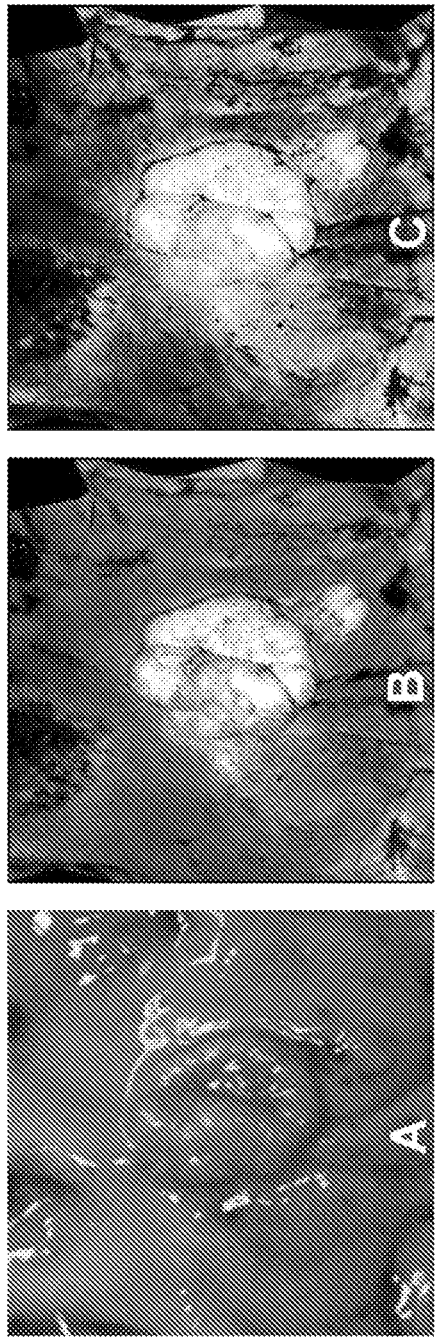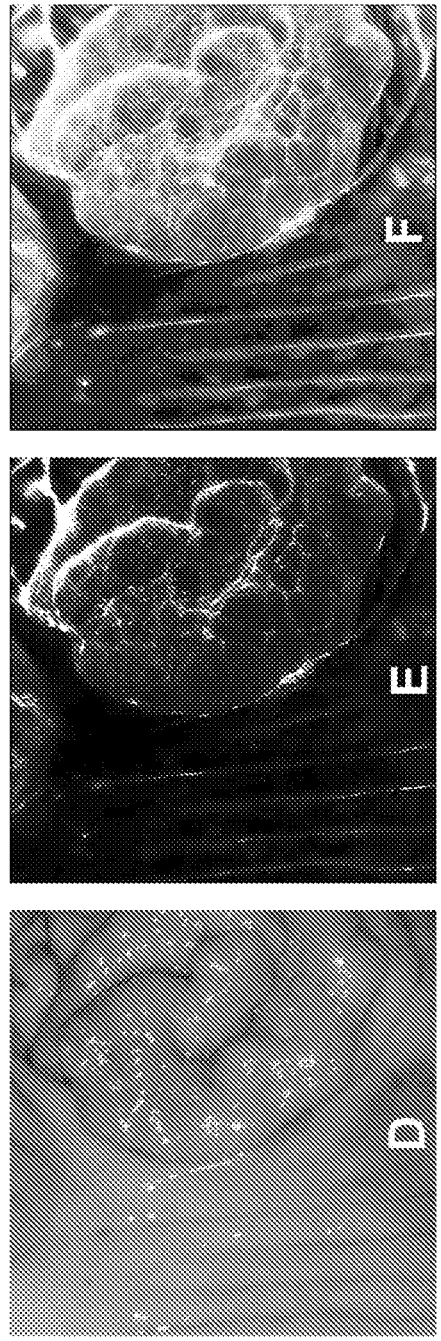

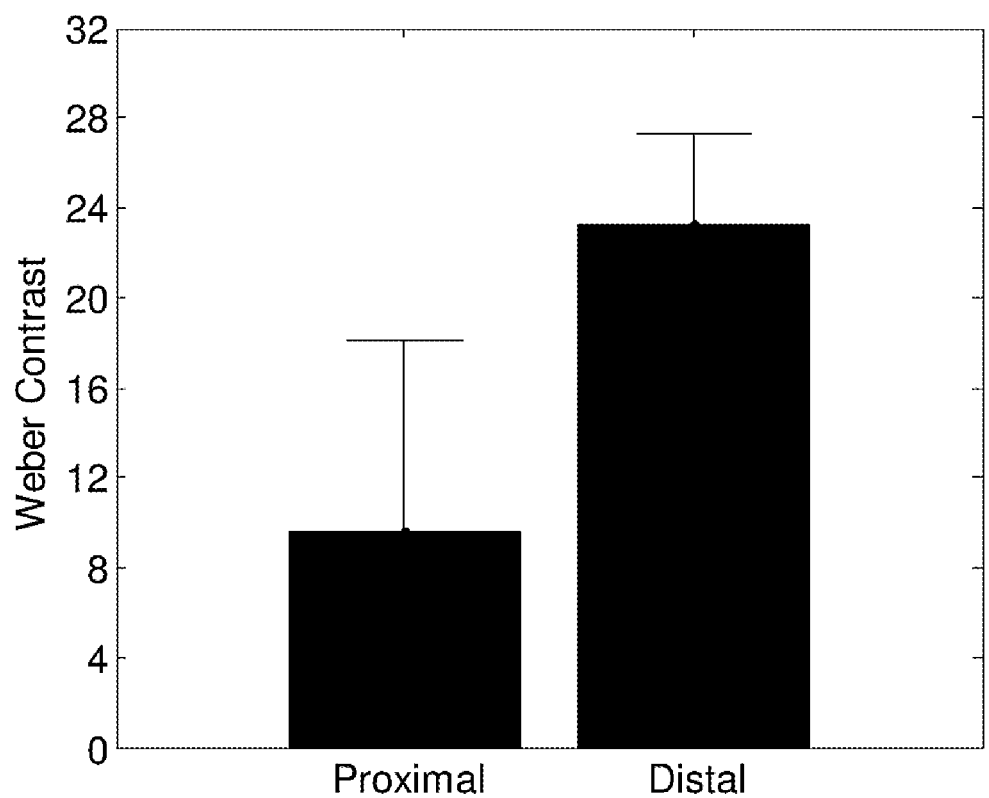

FIG. 15A
FIG. 15B
FIG. 15C
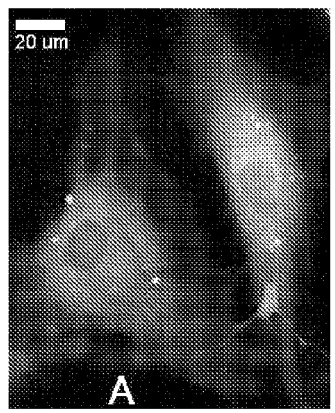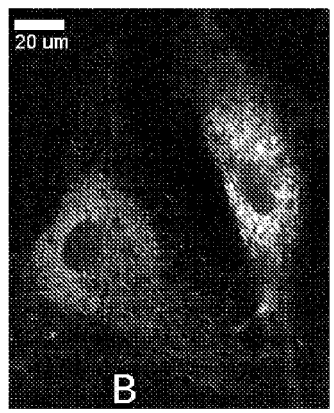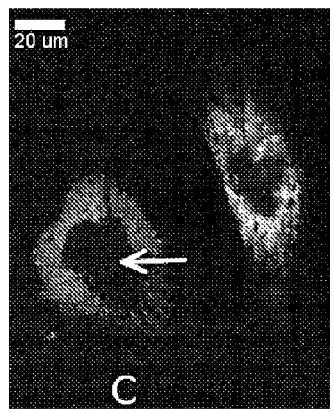
FIG. 16A
FIG. 16B
FIG. 16C
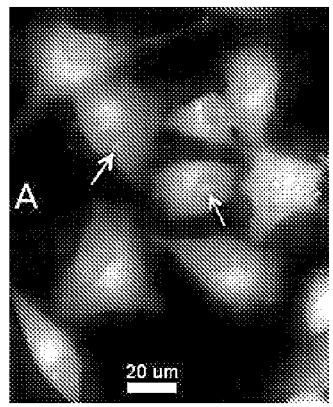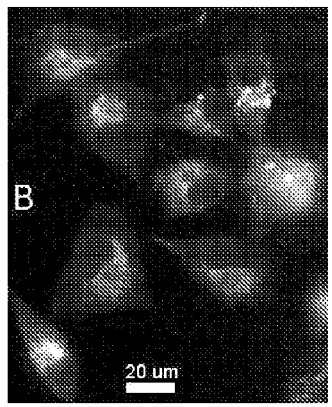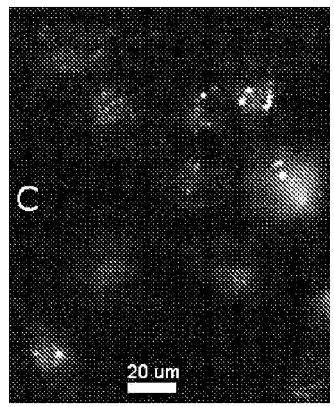
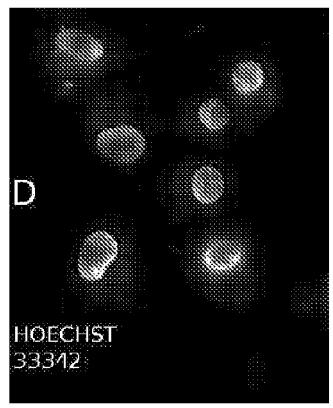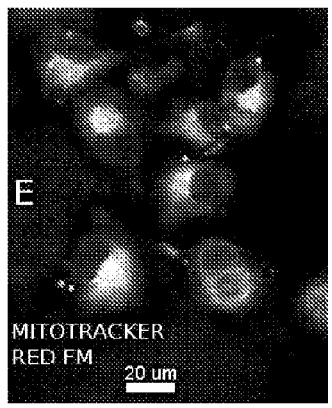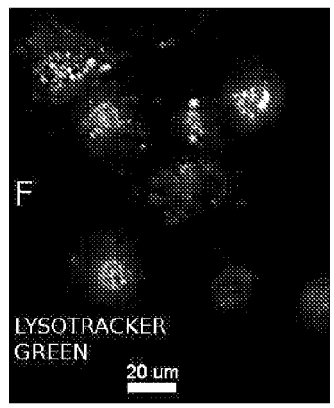
FIG. 16D
FIG. 16E
FIG. 16F

TISSUE IMAGING AND VISUALIZATION OF LESIONS USING REFLECTANCE AND AUTOFLUORESCENCE MEASUREMENTS

CROSS REFERENCE TO RELATED APPLICATIONS

This is the U.S. National Stage of International Application No. PCT/US2013/050753, filed Jul. 16, 2013, which was published in English under PCT Article 21(2), which in turn claims the benefit of U.S. Provisional Application No. 61/849,610, filed Jan. 30, 2013, and U.S. Provisional Application No. 61/741,310, filed Jul. 17, 2012. The provisional applications are incorporated herein in their entirety.

FIELD

This disclosure is related to systems, instruments and methods for imaging using detected fluorescence, reflectance and/or transmittance for the diagnosis of cancer.

BACKGROUND

Prior use of autofluorescence endoscopy has been limited to fluorescence in the visible spectrum with unselected contributions from a number of fluorophores, both cellular and extracellular. Fluorescence has not been so stratified by excitation wavelength to consider the roles played by individual fluorophores. Imaging of cellular fluorophores such as tryptophan has been slowed by limited availability of UV-capable microscope objectives and sub-300 nm light sources.

White light colonoscopy is the preferred screening technique for colon cancer but fails to detect a significant number of polyps and flat neoplasms. Improving the detection rate can help prevent incident cancers and decrease screening intervals, thus improving screening effectiveness while reducing the overall cost. Low contrast lesions (LCLs), including flat lesions such as those having a height less than half their width, are of special concern because they are more frequently cancerous than polypoid lesions. In a recent study, flat cancerous lesions were present in 9.4% of male veterans undergoing colonoscopy. Indigo carmine chromoendoscopy increases the detection of flat neoplasms, but is time consuming for use during screening exams in which a high volume of colonoscopies must be performed under demanding time constraints.

Identifying flat lesions using an endogenous contrast mechanism such as autofluorescence (AF) provides benefits over chromoendoscopy by reducing exam time and eliminating dye toxicity concerns. AF image contrast in tissue is derived from native tissue fluorophores (such as tryptophan, collagen, NADH and FAD) as well as from the effects of absorption and scattering of other components (e.g., hemoglobin). Spectroscopic AF studies comparing normal and neoplastic tissues have consistently noted reduced AF intensity from neoplasms. This general result was obtained in colon tissue at excitation wavelengths including 337 nm, 370 nm, and 442 nm. Discrimination based on reduced AF intensity has put emphasis on correcting AF intensity measurements for variations in absorption, illumination intensity, and tissue surface morphology. It has also drawn attention to methods such as time-resolved AF imaging, which largely avoids the confounding factors for intensity measurements but has its own drawbacks including instrumentation complexity and long acquisition times.

Commercial AF endoscopes for the colon include the AFI system (Olympus Medical Systems, Tokyo, Japan) and PINPOINT system (Novadaq Technologies, Mississauga, ON, Canada; formerly the Onco-LIFE and LIFE-GI system, Xillix Technologies). The first developed was LIFE-GI which illuminated tissue with blue light (400-450 nm) and measured both green AF (490-560 nm) and red AF (>630 nm). Later generations of LIFE-GI have included simultaneous blue and red illumination and ceased collection of red AF in favor of red reflectance (>630 nm). The AFI system illuminates with blue light (395-475 nm) and green light (540-560 nm) in succession and measures green/orange AF (490-625 nm) followed by green reflectance. Both of these commercial endoscopes electronically combine a blue-excited AF image and a reflectance image in a single pseudocolor image presented to the physician. Color differences in the pseudocolor composite image are used to signal the observer to the presence of a lesion. Contrast in images from these endoscopes is produced primarily by a loss of green AF in lesions and is perceived as a changed color ratio. Intensity artifacts due to geometrical shape of the specimen would be apparent in a single image; however, they are reduced in the pseudocolor image because the AF and reflectance images are affected by the same artifacts, preserving the color ratio of the resulting image. Several randomized trials comparing AF endoscopy in the colon to standard video endoscopy, narrow band imaging (NBI), or high resolution endoscopy have been published very recently. The outcomes of these studies have been mixed, with some indicating commercial AF endoscopes can reduce polyp miss rate and others showing no significant improvement of AF over other technologies.

Narrow Band Imaging® (NBI, Olympus Inc. New Hope, Pa.) uses blue and green light that is avidly absorbed by hemoglobin and displays blood vessels with high contrast and enhances the visualization of superficial mucosa. Flexible Spectral-Imaging Color Enhancement (FICE®, Fujinon Inc., Wayne, N.J.) uses white light illumination followed by spectral estimation to produce high contrast images. However, neither NBI, FICE or I-Scan® (Pentax Medical Co, Montvale, N.J.) have been shown to improve the detection rate of neoplasms compared to high resolution white light endoscopy.

When light illuminates the mucosa, it is largely reflected and scattered. Some of it is absorbed and re-emitted at a longer wavelength by molecules in tissue (fluorophores) to produce fluorescence of a redder color than the illuminating beam. Fluorophores are inherent biological compounds that emit light, most notably metabolic co-factors such as NADH and FAD, amino acids such as tryptophan, structural proteins such as collagen and elastin as well as porphyrins. Early measurement systems relied upon broadband autofluorescence with unselected contribution from NADH, FAD, collagen and elastin. Initial work with fiberoptic instruments showed reduced fluorescence with neoplastic change. Auto-Fluorescence Imaging (AFI) (Olympus Inc. New Hope, Pa.) is an endoscopic autofluorescence system using blue light excitation in the 400-500 nm wavelength range to produce autofluorescence at 490 to 625 nm. A reflectance image of the mucosa is then taken with green light (550 nm). A pseudocolor (magenta) is computed to show the areas of decreased fluorescence and the surrounding normal mucosa appears green from the reflected light, with the blood vessels appearing dark green. The Onco-Life system (Xillix Technologies Corporation, Richmond, BC, Canada) uses blue light (400-450 nm) for excitation, captures fluorescence from 490 nm to 560 nm and combines it with a red reflectance image. The results from the existing autofluorescence endoscopes have been mixed, with some showing increased detection of polyps, while others showed no improvement over white light endoscopy with missed detection of flat lesions.

Techniques such as enhanced backscattering spectroscopy, partial-wave spectroscopic microscopy and karyometry can be used for risk stratification but are still dependent on standard white light colonoscopy for the detection of neoplasms.

A need exists for optical techniques and instrumentation that sufficiently enhances the image contrast of LCLs, so that the latter can be easily seen and not missed, even during a busy endoscopy schedule or at the end of the queue. The ideal solution preferably highlights the presence and location of a neoplasm, including those that are difficult to see with the naked eye, without dependence on labels or other exogenous chemicals. There is also a need for a technique that highlights the presence of neoplasms conveniently such as by turning on a switch. Finally, a need exists for a multispectral imager with UVC excitation and detection capability, including sub-300 nm excitation.

SUMMARY

Methods and systems are disclosed that use fluorescence, reflectance and/or transmittance in conjunction with use of selected ratiometric formulae to produce images of diseased tissues and cells with high contrast. High contrast facilitates identification of the diseased tissue and cells. The systems and associated methods disclosed herein can, in some examples, provide excitation in the mid and/or deep ultraviolet range, including excitation wavelengths less than 300 nm. In some instances, observation of the fluorescence also occurs in the ultraviolet range. Moreover, whereas AFI and OL images display both reflectance and fluorescence in separate color channels without integration and have variable performance due to dependence on unselected cellular and extracellular fluorophores and indeterminate effects of absorption and scattering, the techniques disclosed herein target specific fluorescence signals that produce the greatest contrast (such as fluorescence from tryptophan, FAD, NADH, elastin and/or collagen) while reducing or minimizing effects of absorption and scattering. While the disclosed methods and systems have been demonstrated on in vitro surgical specimens, it has been shown that in-vivo fluorescence results may in fact be superior to in-vitro methods and apparatus.

In a preferred embodiment, ratiometric fluorescence (FR) imaging methods and systems selectively use multiple signals for the detection of a condition such as a neoplasm. Synthetic formulaic images are computed to provide enhanced or maximized contrast between normal and abnormal species within the sample. Abnormal species refers to diseased tissue including but is not limited to cancer, pre-cancer, fibrosis, inflammation, ischemia, mutation or express unregulated behavior (with or without mutation).

In some embodiments, the methods and systems disclosed herein for detecting changes in protein concentrations and/or disease states use targeted autofluorescence of specific native fluorophores found in tissue such as that found, for example, in the colon, the esophagus, the oral cavity, the pancreas, the cervix and the lung. This unique method of image formulation based on expected structural and molecular changes associated with neoplastic transformation may permit improved endoscopic imaging that improves detection of lesions which may be difficult to see and/or missed due to endoscopist inexperience and/or endoscopist independent factors such as poor contrast compared to the surrounding mucosa. Significantly, the FR imaging techniques disclosed may increase detection of serrated and/or flat lesions that are encountered in the colon such as in the proximal colon.

Implementations of the disclosed methods in video rate or still imaging provides increased image contrast between diseased tissue (lesions) and surrounding normal tissues, or between two different disease processes (such as cancer and inflammation), or between different grades of disease such as cancer, high grade dysplasia and low grade dysplasia (pre-cancer). Synthetic formulaic images are computed with the goal to provide increased contrast between lesions and surrounding normal tissue. As used herein, lesion refers to diseased tissue that includes but is not limited to cancer, pre-cancer, fibrosis, inflammation and ischemia. When implemented in endoscopy, such computed formulaic images provide enhanced lesion contrast, exceeding the contrast for normal white light visual observation without the need for labeling or manipulation of the tissue in a real-time manner. In typical examples, imaging methods are based on three or more excitation beams using near-UV or mid-UV excitation. Methods and systems can use combinations of green and blue fluorescence with reflectance, to provide effective contrast enhancement using division, multiplication, subtraction and additions of individual images intensities. The disclosed approaches are not dependent on use of dyes; permit real time computation of formulaic images, are integrable into endoscopes; provide superior imaging of flat lesions that are easily missed in conventional approaches, and provide well defined lesion borders. In some examples, precancerous lesions of the cervix or oral cavity, or adenomas or adenocarcinomas in colon specimens are identified. In some examples, an agent is administered to treat, prevent or ameliorate the disease state which is diagnosed. Other applications include microscopy, colonoscopy and sigmoidoscopy.

BRIEF DESCRIPTION OF THE FIGURES

In FIG. 2, the illumination light path is from bottom to the top of diagram. Optical elements have high transmission in the sub-300 nm range of interest except for the UV objective which has very low transmission below 340 nm.

FIGS. 8A and 8B are scatter plots showing performance of an optimized contrast metric (Equation 2) and the Weber contrast metric, respectively, for measurement of contrast in ratiometric images produced by an exemplary ratiometric imaging system. The metrics are assessed by comparing against visually assessed contrast. Each data point represents a single ratio image of a particular specimen. Linear fits to the data indicate that the optimized metric is typically a better indicator of useful contrast in ratio images than the Weber contrast.

FIGS. 9A-9F are images showing the effects of autoscaling and histogram equalization on display ratio images formulated by the exemplary ratiometric imaging system. FIG. 9A is a standard photograph of a first adenoma taken with digital SLR camera. FIG. 9B is an autoscaled R27 ratio image of the first adenoma. FIG. 9C is a histogram equalized R27 ratio image of the first adenoma. FIG. 9D is a second adenoma from another specimen imaged by digital SLR camera. FIG. 9E is an autoscaled R7 ratio image of the second adenoma. FIG. 9F is a histogram equalized R7 ratio image of the second adenoma. Images A, B, and C demonstrate that autoscaling of ratio image R27 is more effective than histogram equalization, while D, E, and F show the benefit of histogram equalization for ratio image R7. Tattoo ink applied prior to excision caused the dark color artifacts in images A (immediately left of polyp) and D (bottom center of image).

FIG. 14 is a bar graph showing contrast levels for proximal and distal lesions achieved by the exemplary ratiometric imaging system disclosed herein using novel formulaic ratio images.

FIGS. 15A-15C are autofluorescence images of hTERT-HPNE cells excited at A) 280 nm, B) 370 nm, and C) 440 nm. FIG. 15A shows the ability to clearly visualize entire cells. The arrow in FIG. 15C shows an area of difference compared the other images including FIG. 15B.

FIGS. 16A-16F are autofluorescence images of MIA PaCa-2 cells excited at A) 280 nm, B) 370 nm, and C) 440 nm; and fluorescent probe images (D-F) taken following 4 minutes incubation in a multicolor stain. Nuclei are visible as darker regions of cells in both FIG. 16A and FIG. 16B. FIG. 16A shows bright nucleoli, two of which are designated with arrow. FIG. 16B shows a string or mesh-like pattern characteristic of mitochondria and corresponds with the MitoTracker stain in FIG. 16E. Fluorescent probe images reflect that a few cells (3 o'clock, 8 o'clock positions) detached during media exchange. Note the similar appearance of FIG. 16C to the LysoTracker stain in FIG. 16F.

DESCRIPTION OF EMBODIMENTS

Figure 1:
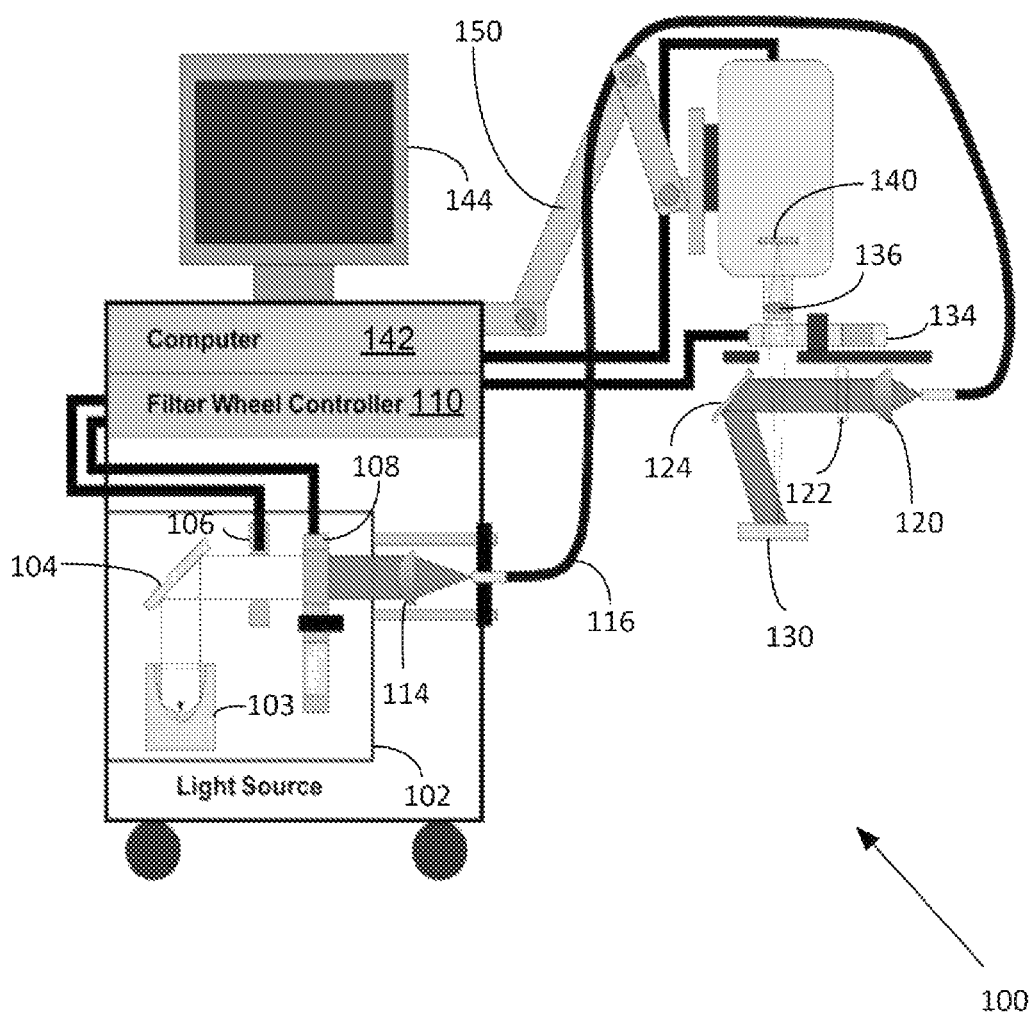
FIG. 1 is a simplified schematic diagram of a representative multispectral imaging system.

All publications, patent applications, patents, and other references mentioned herein are incorporated by reference in their entirety for all purposes.

Although methods and materials similar or equivalent to those described herein can be used to practice or test the disclosed technology, suitable methods and materials are described below. The materials, methods, and examples are illustrative only and not intended to be limiting.

The singular forms "a," "an," and "the" refer to one or more than one, unless the context clearly dictates otherwise. For example, the term "comprising a specimen" includes single or plural specimens and is considered equivalent to the phrase "comprising at least one specimen." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

I. Definitions

In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Adenoma: A collection of neoplastic cells of glandular origin that has not yet acquired the ability to invade the basement membrane of the sub-mucosal tissue.

Adenocarcinoma: An adenoma that has acquired the ability to invade the basement membrane of the sub-mucosal tissue.

Autofluorescence: Fluorescence emitted by a native fluorophore.

Cancerous: Neoplastic cell/tissue growth of any type, including benign or malignant growths of glandular (e.g., adenoma, adenocarcinoma) or non-glandular origin.

Contrast: A difference in luminance associated with a tissue image that makes a lesion in the image distinguishable from surrounding tissue.

Diagnostic: Identifying the presence or nature of a biological or medical condition, such as, but not limited to, presence of a genetic mutation, systemic or localized concentration in a subject of an administered pharmaceutical composition, occurrence of dysplastic nevus syndrome, or occurrence of melanoma.

Excitation Signal: Optical radiation at a selected wavelength or wavelength range for producing fluorescence, reflectance and/or transmittance.

Fluorescence: Emission of longer wavelength (lower frequency) photons (energy) by a molecule that has absorbed photons (light) of shorter wavelengths (higher frequency). Both absorption and radiation (emission) of energy are unique characteristics of a particular molecule (structure) during the fluorescence process. Light is absorbed by molecules causing electrons to become excited to a higher electronic state. The electrons remain in the excited state for a very short period, and then, assuming all of the excess energy is not lost by collisions with other molecules, the electron returns to the ground state. Energy is emitted during the electrons' return to their ground state.

Image: Refers to a viewable image for direct viewing by a human observer, a projected image to be directed to a detector, or a stored representation of such an image such as a digital data file.

Native Fluorophore: A naturally occurring compound or substance within a subject that emits fluorescence in response to an excitation signal. A fluorophore may be a chemical compound, polypeptide, protein or other molecular element, or any part thereof. Of particular interest herein are those native fluorophores that exhibit an association with neoplastic transformation in a tissue of an organ such as the colon. These native fluorophores exhibit an increased or decreased fluorescence in association with a neoplastic process occurring in the vicinity of the fluorophore. Such an association may reflect an underlying positive or negative correlation with the neoplastic process, such as increased or decreased abundance and/or bioactivity of the fluorophore. Exemplary native fluorophores include, without limitation, tryptophan, collagen, NADH, FAD, collagen, elastin, lipofuscin, porphyrins, phenylalanine and tyrosine. Native fluorophores exhibiting an established association with neoplastic transformation include, without limitation, tryptophan, FAD, NADH and collagen. Fluorescence emitted by such fluorophores is referred to as native fluorescence.

Optical Radiation: Propagating electromagnetic radiation having wavelengths between 100 nm and 1000 nm. Optical radiation at wavelengths between 400 nm and 700 nm is also referred to as illumination.

Preventing, Treating or Ameliorating a Disease: Preventing a disease refers to precluding the onset or inhibiting the full development of a disease such as melanoma and is a form of prophylaxis. Treating refers to a therapeutic intervention that ameliorates a sign or symptom of a disease or pathological condition such as melanoma after it has begun to develop. Ameliorating refers to the reduction in the number or severity of signs or symptoms of a disease, such as cancer.

Ratiometric Formula (RF): Any formula involving a ratio (a quantity divided by another quantity) which is used to calculate intensity values for a ratiometric image based on measured fluorescence and/or reflectance data. The ratiometric formula will generally have at least one fluorescence or reflectance value but may have one, two or multiple measured values in the numerator or denominator. The ratio may be, for example, simply the inverse of a fluorescence or reflectance value.

Ratiometric Image (or Ratio Image): An image produced in accordance with a ratiometric formula wherein the intensities produced along the image are in proportion to ratios calculated based upon fluorescence/reflectance determined for various points along the image.

Reflectance: A ratio of the optical power actually exiting a sample (such as a tissue portion) under study to the amount that would exit if none were absorbed. Reflectance is typically considered to be unit-less. Reflectance spectroscopy can be combined with fluorescence spectroscopy (see WO 1999057529 A1, which is incorporated herein by reference).

Sample: A biopsy, serum, blood, plasma or other substance from an animal (e.g., human) that includes biomolecules and antibodies representative of those present in the animal. Samples can include processed tissue samples, blood samples, secretions, and the like. A sample can be an unharvested tissue located within the body of a subject which may or may not be subjected to one or more visual inspections and/or biochemical assays. As another example, a sample may be tissue from a nevus harvested during a biopsy which also may optionally be subjected to one or more visual inspections and/or biochemical assays.

Subject: Living multi-cellular vertebrate organisms, a category that includes both human and veterinary subjects, including human and non-human mammals.

Weber contrast: A metric which may be used to quantify contrast within images. Weber contrast is defined as the absolute value of the difference between the luminance of a lesion or other image feature and the luminance of the background which is then divided by the luminance of the background. Mathematically, Weber contrast is represented as: $|(I-I_b)|/I_b$, where I is the luminance of the selected feature and $I_b$ is the luminance of the background. If parameters are set such that the luminance of a cancerous lesion or other feature is higher than the background, the Weber contrast formula is simply the difference between the luminance of the lesion and the luminance of the background which is then divided by the luminance of the background. Mathematically, this is represented as: $(I-I_b)/I_b$ Contrast may also be calculated using other metrics, including the optimized contrast metric disclosed herein.

II. Imaging Methods and Instrumentation

Methods and systems based on use of ratiometric fluorescence imaging for the diagnosis and characterization of disease are disclosed herein. A representative spectral imaging system is configured to produce autofluorescence and/or reflectance images by irradiating a sample illuminating and detecting reflected, scattered, or fluorescence radiation over a range of wavelengths, such as irradiation from 260 to 650 nm and detection from 340 to 650 nm to collect visual information, including both video and still images of tissues. In various embodiments, irradiation be over wavelengths between 200 to 700 nm and detection may be over wavelengths between 300 and 800 nm. The area imaged may be narrow or macroscopic (e.g., 40 mm by 40 mm). The specimen may be in vitro (i.e., resected tissue) or in vivo. The tissue may be imaged at a surface of the tissue without special labels, exogenous chemicals and/or other manipulation of the tissue. In some embodiments, a portion of the tissue which is not located at the surface is imaged, either by manipulation of the specimen to expose said portion or by physical penetration of the specimen using the endoscope or other apparatus within the system which comprises or is connected to the imager.

The imaging system comprises a light source which can produce monochromatic or polychromatic optical radiation. If a polychromatic tight source is used, a bandpass filter may be attached. The bandpass filter may allow optical radiation at one or more frequencies, by transmission, reflection, diffraction or other process to pass through. The frequencies associated with the light source are selected to elicit data diagnostic of a tissue condition, in various embodiments, the light source emits optical radiation at a frequency chosen to excite a native fluorophore to emit a fluorescence signal. In various embodiments, the light source emits light at a frequency chosen to elicit reflectance from a sample. A wide variety of light sources may be used, including but not limited to a xenon lamp.

The imaging system also comprises a detector which may further comprise, for example, a photomultiplier tube, a photosensitive diode, a charge coupled device, or any other type of electromagnetic radiation sensor. In one example, detectors charge coupled device and/or could be located at a distal end of an endoscope or catheter instrument. The charge coupled device is coupled to an image processor. If the detector is not a charge coupled device located at a distal end of an instrument, the returned electromagnetic radiation may be conducted to the detector through one or more return optical fibers. The return optical fibers and the excitation optical fibers may be co-located within the same instrument, or they may be located in separate instruments. Alternately, the same optical fibers within an instrument may be used to perform both excitation and return functions. In certain embodiments, the detector may be in communication with a downstream microprocessor through a wired or wireless data connection.

With reference to FIG. 1, a representative imaging system 100 includes a light source 102 configured to produce one or more excitation beams at selected wavelengths or wavelength ranges. The light source 102 includes a xenon lamp 103 (or other radiation source) that couples an optical radiation beam to an ultraviolet cold mirror 104 configured to transmit infrared radiation and reflect ultraviolet radiation so as to reduce infrared power in an excitation beam. The optical radiation beam is then directed to a shutter 106 and a first filter wheel 108 that includes one or more optical filters configured to provide a selected spectral content for an excitation beam. The shutter 106 and the first filter wheel 108 are coupled to a filter wheel controller 110 that is configured to insert a suitable optical filter into the optical radiation beam and to block or unblock the optical radiation beam with the shutter 106.

A lens 114 couples the optical radiation beam into a fiber bundle 116, typical a quartz fiber bundle. The fiber bundle 116 delivers the optical radiation beam to a beam shaping lens 120 and an ultraviolet polarizer 122. A mirror 124 directs the optical radiation beam as an excitation beam to a specimen 130.

Radiation from the specimen 130 and responsive to the excitation beam is coupled through a second filter wheel 134, and an imaging lens 136 forms an image of at least a portion of the specimen 130 or specimen surface at a CCD or other detector 140. The detector 140 is coupled to an image processor 142 that is configured to perform ratiometric calculations based on detected image intensities in selected regions of interest, and provide suitable images for viewing at a display 144. In some cases, processed images are delivered for remote viewing via a local or wide area network or the internet, or images from the detector 140 can be communicated to a remote location for ratiometric processing. As shown in FIG. 1, the excitation beam and imaging optical system are secured to a mechanical arm 150 so that images of specimens at a plurality of locations or different locations on the same specimen can be obtained.

A representative prototype imaging system for measuring AF and reflectance as shown in FIG. 1 can be implemented as follows. Diffuse reflectance images are collected using a pair of crossed UV polarizers (available at Meadowlark Optics, Frederick, Colo.) to minimize specular reflections. The light source may be a xenon arc lamp system (e.g., 300 W, Lambda LS, available at Sutter Instruments, Novato, Calif.) which may have a built-in filter wheel such as a ten-position filter wheel. Use of a full-spectrum bulb allows significant output in the 260-300 nm range but may necessitate a UV cold mirror (Chroma, Bellows Falls, Vt.) with high reflectance in the same range and/or an ozone filter (Oriel Instruments, Irvine, Calif.) to eliminate health risks from ozone produced by interaction of UVC light with air. The purpose of the UV cold mirror is to remove near infrared light which can be damaging optical filters. A first filter wheel and controller (Lambda 10-3, Sutter Instruments, Novato, Calif.) is provided to allow automated selection of illumination and/or detection wavelengths via interference filters. A fiber bundle (FiberTech Optica, Ontario, Canada) which may be a custom quartz material delivers filtered illumination from the lamp to the specimen, and fused silica lenses perform light coupling and collimation. The fiber bundle may comprise a feedback fiber for monitoring lamp power fluctuations. A thermoelectrically cooled, UV-enhanced camera (PhotonMAX: 512B, Princeton Instruments, Trenton, N.J.) with intensified CCD (e2v CCD97B, e2v technologies, Chelmsford, England) is mounted on a rigid mobile arm and equipped with UV-transmitting and color-corrected imaging lens (f/3.5, f=63 mm, Resolve Optics, Chesham, UK) with a fixed working distance of 25 cm. A second ten-position filter wheel (H) is mounted directly in front of the imaging lens. An interface may be used to control system components including filter wheels, mechanical shutter, and image acquisition. In an embodiment, automation via scripting allows for rapid sequential capture of a multitude of images of interest (and their corresponding dark frames) in a short time period such as in about 90 seconds.

The optical radiation provided to the specimen be narrowband, such as ~20 nm full width half maximum (FWHM), and accomplished with band-pass interference fillers. Optical radiation from the specimen associated with reflection or fluorescence may be coupled to a detector via longpass or other optical filters. In some examples, the short wavelengths may require special optics as the transmittance of standard optical materials is often limited at wavelengths shorter than about 380 nm.

Long-pass filters may be selected to enable collection of weak AF using very short exposure times. Optical radiation for diffuse reflectance images is preferably passed through a drop-in UV polarizer and collected through a second UV polarizer mounted in the emission filter wheel. AF contributions to reflectance images are generally neglected because contributions are typically 1000 times less than reflectance contributions.

Excitation wavelengths and emission bands of AF images can be chosen to target native fluorophores (such as tryptophan, collagen, NADH, FAD, collagen, elastin, lipofuscin, porphyrins) whose concentrations and/or distributions can change with disease state such as a cancerous process. In one embodiment, one or more native fluorophores exhibit a change (such as a change in concentration, distribution or activity) in association with a cancerous process. This cancerous process may be malignant or benign, and may specifically involve the colon, such as the proximal and/or distal colon. The cancerous process may specifically be an adenocarcinoma or adenoma (including a tubulovillous adenoma). In an embodiment, the one or more native fluorophores exhibit a change (such as a change in concentration, distribution or activity) in association with an inflammatory process Six exemplary diffuse reflectance image types collected by the system disclosed herein are listed in Table 1. These are crossed polarization images using narrow band illumination (20 nm FWHM) centered at wavelengths specified in the image names. They range from R370 in the UV to R555 in the green with maximum absorption by hemoglobin in the blue (400-450 nm).

TABLE 1

Reflectance images with names specifying illumination wavelength

| Name | Color |
|---|---|
| R370 | UVA |
| R400 | Violet |
| R415 | Violet |
| R440 | Blue |
| R480 | Blue-Green |
| R555 | Green |

For excitation filters, percent transmission outside of the desired illumination band is desirably $10^5$ times lower than the peak transmission inside this band. Two or more filters may be stacked to achieve this condition. System bandpass excitation filters may possess out-of-band attenuation 4 to 5 orders of magnitude greater than in-band. Relative attenuation may be greater as this measurement is limited by the dynamic range of the spectrophotometer. Longpass emission filters preferably show attenuation 5 orders of magnitude below the cut-on wavelengths. Narrowband illuminations, including 320, 340, and 440 nm, may reveal no measurable out-of-band light (indicating at least 5 orders of magnitude less out-of-band illumination). For example, the 280 nm narrowband illumination may produce no measurable out-of-band light aside from a spectral feature at 825 nm that is 4.4 orders of magnitude below peak intensity. In some embodiments, an additional shortpass filter (FF01-680/SP, high transmission 345 to 655 nm, Semrock Inc., Rochester, N.Y.) may be placed, transiently or permanently, in front of the camera's imaging lens to eliminate the influence of small amounts of NIR illumination which may leak through excitation filters.

In various embodiments, the ratio imaging techniques disclosed herein may be incorporated in an advanced endoscope for use in disease screening, including colorectal cancer screening. The FR system can be built into endoscopes which may be configured to provide, in certain embodiments, simultaneous and/or real-time imaging side by side with white light endoscopy for in vivo applications. For example, the FR system can be incorporated into endoscopes to provide real-time images of the colon that would indicate the locations of neoplasms without the use of dyes, ligands, or antibodies and lead to higher detection rates of colonic neoplasms. The FR system can also be integrated into probes which can be passed through endoscopes. In an embodiment, the FR system can be readily added on to an existing video endoscope system. In an embodiment, a shutter is provided in the optical path of the endoscope's visible light source. While the approach disclosed herein would increase sensitivity and efficacy of endoscopy, it is broadly applicable to any type of optical tissue imaging. In an embodiment, the disclosed methods do not utilize peptides or ligands to bind to regions of interest within a lesion. This has a distinct advantage of avoiding the time and cost associated with ligands, dye or antibodies.

Such FR systems can also be integrated into microscopes, such as a standard upright microscope, to examine cells such as those obtained in a needle or other biopsy. This approach provides a basis for a diagnostic test using fluorescence microscopy to interrogate cells obtained. In an embodiment, UV excitation fluorescence microscopy is applied to fluorophore imaging in tissue using, for example, at least one mid/deep UV wavelength (e.g. 280 nm) to image at least one fluorophore such as tryptophan in primary and/or cultured cells such as epithelial cells and/or those from a solid organ (e.g., pancreas). In one embodiment, the fluorescence microscopy can determine fluorescence generated by a fluorophore(s) in response to excitation signal(s) in a particular cluster of cells and/or within an individual cell. In various embodiments, such fluorescence microscopy can differentiate fluorescence based on the specific intracellular source such as mitochondria, the nucleus, cytosol, secretory granule, lysosome or a nucleolus. For example, when applying such imaging technology to fluorescence imaging of cells, imaging at F300 (250-300)/(300-400) outlines cells with intensity levels varying in accord with cellular protein production. Cancer cells may express a bright nucleolus which may be indicative of dysregulated ribosome synthesis. Excitation/emission imaging of (340-360)/(400-500) and (400-450)/(500-560) are related to mitochondrial activity and lysosomes, respectively.

The microscopy system may comprise an imaging chamber which may be filled with imaging media. The chamber may further be filled with a stain media for staining adherent cells on the microscope stage. The stain media may permit easier visibility of autofluorescence and/or identification of AF originating from specific intracellular locations. The cell autofluorescence may be imaged before and/or after addition of the stain media. Where AF is imaged both before and after addition of stain media, the entire process of cell microscopy may be completed in under about 10 minutes, such as in about 7 minutes. Paraffin or other soft solid may be placed at ends of the imaging chamber (which may be located towards the center of a slide). The imaging chamber may be connected to compartment(s) comprising imaging and/or stain media via a syringe and tubing. The imaging chamber may further comprise air intake and outlet.

Biopsied cells might be excited at one wavelength, for example at 280 nm excitation, for discrimination based on protein content/distribution, such as that of tryptophan, with additional metabolic information gained using longer UV wavelengths to excite at least one other fluorophore (e.g., NADH and/or FAD). For example, 340 to 380 nm excitation wavelengths are used to excite NADH. Likewise, blue wavelengths (430 to 480 nm) may be used to excite FAD. Combined information using fluorescence from multiple fluorophores may be expected to provide multiple levels of confirmation and thus a more a reliable diagnosis than single excitation wavelength images.

Figure 2:
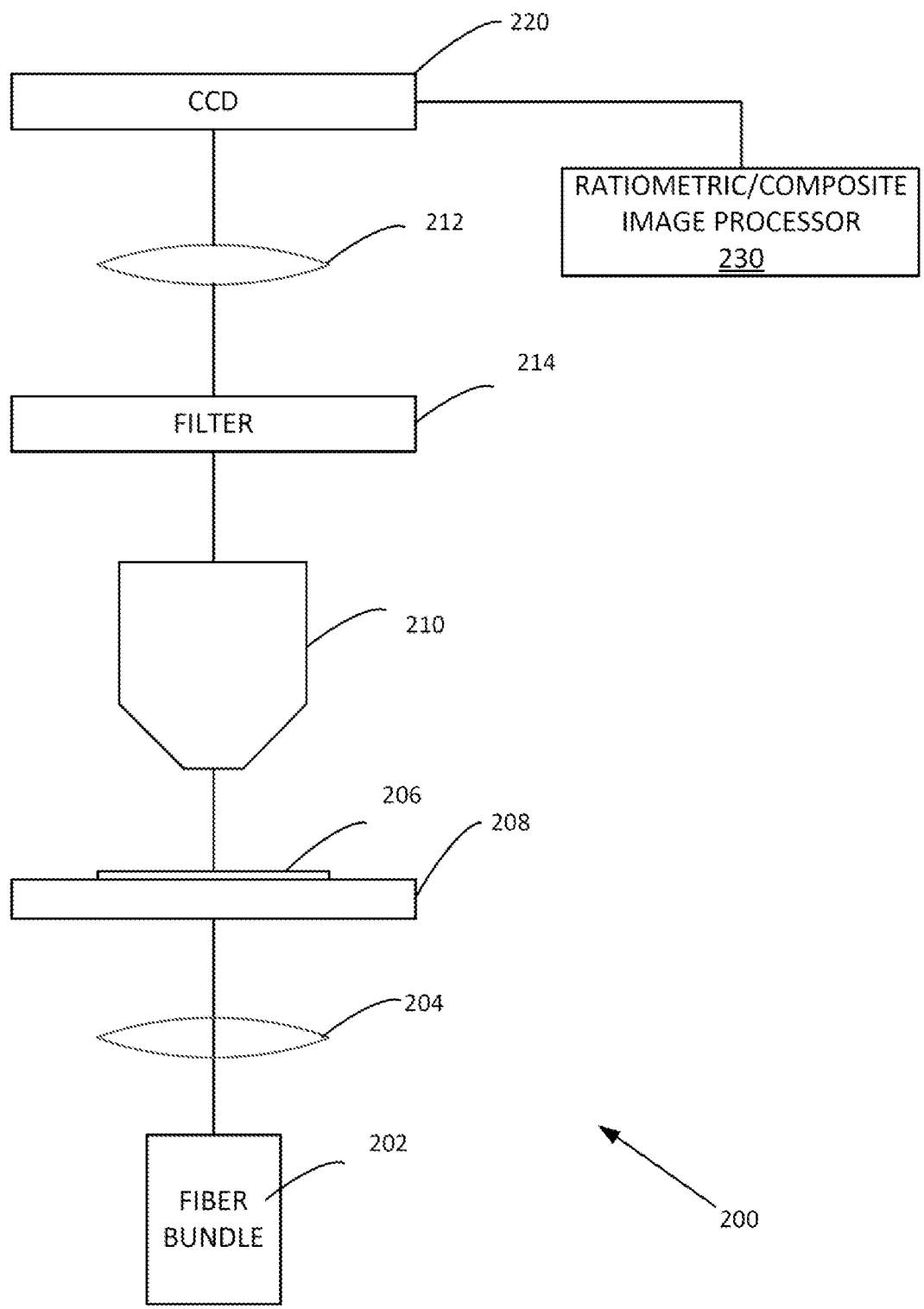
FIG. 2 is a simplified schematic diagram of an exemplary UV autofluorescence microscope in an upright transillumination configuration.
Figure 3:
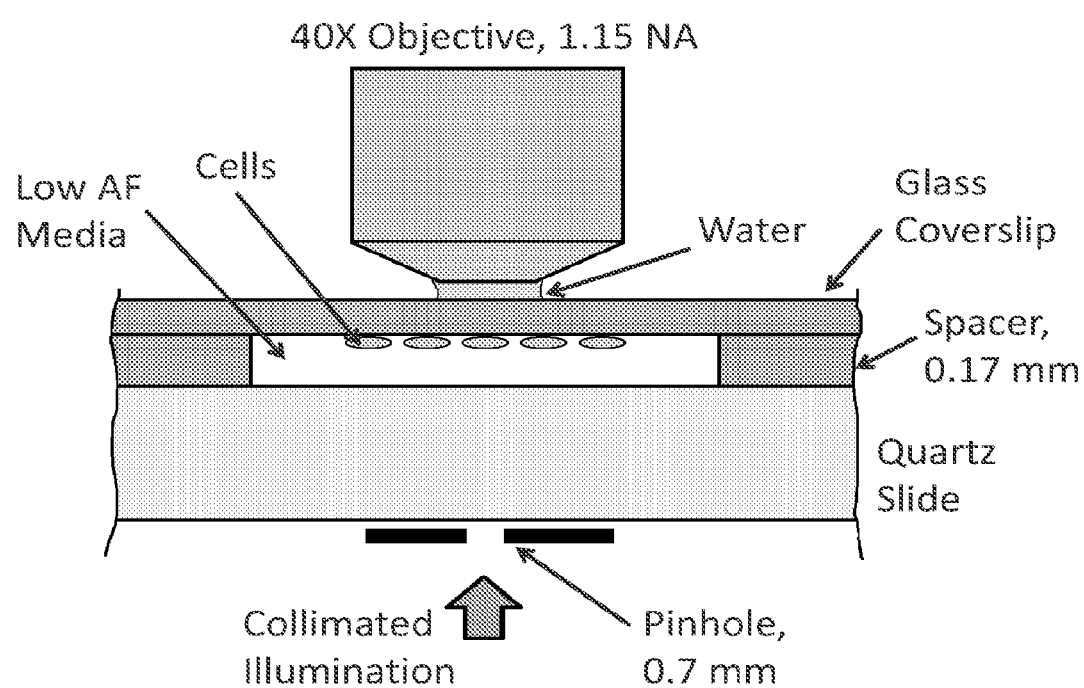
FIG. 3 is a simplified schematic diagram showing an arrangement for cell AF imaging in transmission mode using an upright microscope. Cultured cells are immersed in low AF media (HBSS & L-glutamine). Stage and objective heaters (not shown) maintain specimen temperature within 2 degrees of 37° C. Suspension cells are also imaged in this setup but settle and rest on the surface of the quartz slide.

With reference to FIG. 2, a representative ratiometric analysis system 200 based on a microscope configuration includes a quartz fiber bundle 202 that is configured to deliver an optical excitation beam to a sample 206 that is situated on a quartz substrate 208 via an excitation beam shaping lens 204. A quartz or other UV appropriate lens 204 couples the excitation beam to the sample 206. An objective lens 210 such as a UV objective that is infinity corrected and an auxiliary objective lens 212 form an image of the sample 206 at a detector 220 based on optical radiation responsive to the optical radiation beam. In some examples, optical radiation received via one or more of fluorescence, reflectance, transmittance, scattering, refraction, or diffraction is used in image formation. An emission filter 214 is situated to provide suitable spectral filtering. Images from the detector 220 are coupled to a ratiometric processor 230 that produces processed images based on variety of ratios. In FIG. 2, a transmitted light configuration is illustrated, but other configurations such as an incident light configuration can be used.

In an exemplary AF microscopy embodiment such as shown in FIG. 2, imaging hardware adapted for UV in the transillumination configuration is provided. Autofluorescence microscopy may be performed in a transillumination configuration using multiple excitation wavelength bands (such as bands centered at 280 nm, 370 nm, and 440 nm). Low transmission of shorter wavelengths (e.g., 280 nm light) can prevent the use of a standard epi-illumination configuration to capture deep UV transmission images. This exemplary embodiment includes a UV objective such as a water immersion infinity-corrected objective, a quartz tube lens, quartz collimating lens, quartz optical fiber bundle, and an image detector capable of detecting UV and blue/green visible light such as a scientific-grade CCD with enhanced UV sensitivity. The objective capably provides sufficient transmission of UV light within the emission band of tryptophan (30% at 340 nm up to 80% at 380 nm) and good transmission (>80%) from 380 nm to 760 nm.

Other microscopy systems can use reflecting objectives that are transmissive at ultraviolet and/or visible and/or infrared wavelengths.

A full-spectrum xenon arc lamp may deliver filtered illumination via the quartz optical fiber bundle, with fluorescence imaging enabled by emission filters manually inserted in the collimated light path above the microscope objective via a custom slide-in holder. Cells can be imaged on quartz slides possessing high transmission at shorter wavelengths such as around 280 nm. Cell viability can be maintained by heating the stage and objective to 37° C. Image acquisition may be automated such as by computer control of the CCD, excitation filter wheel and/or light source shutter.

Excitation and emission filters may be selected for the target fluorophores. In various embodiments, two or more excitation filters and two or more emissions filters may be provided. For example, sub-300 nm imaging may use two excitation filters (e.g., 280/20 bandpass, Semrock; 280/17 bandpass, Chroma) and two emission filters (e.g., 360/40 bandpass, Chroma; 300LP longpass; Chroma). Imaging at around 370 nm illumination (which may target NADH) may employ three excitation filters (e.g., 2×370/36 bandpass, Semrock; UG11-1 mm, Schott) and two emission filters (e.g., 447/60 bandpass, Semrock; 409LP longpass, Semrock). 440 nm illumination (which may target FAD) can include two excitation filters (e.g., 440/21 bandpass, Omega; 438/24 bandpass, Semrock) and two emission filters (e.g., 560/70 bandpass, Chroma; 520LP longpass, Chroma).

Various steps may be taken to reduce the background signal in fluorescence images. Excitation filters, such as two or more filters, may be used at each illumination band to increase out-of-band optical density (OD). This light may be rejected using an additional bandpass filter placed after the fiber bundle, as required. In the transillumination configuration, light passes through the sample and may excite AF in the objective lens. This AF may be reduced by limiting spatial extent of sample illumination with a field aperture (e.g., a 700 micron pinhole) located immediately below the quartz slide. The aperture may be aligned (centered on the field-of-view) prior to cell imaging. Standard glass coverslips may be used for imaging instead of quartz, and may further act as a long pass filter suppressing 280 nm excitation light. While standard coverslips may fluoresce in response to 280 nm, their emission may exceed 380 nm and thus may be beyond the region in which AF from certain fluorophores (e.g., tryptophan) is collected.

Target fluorophores can include any fluorophore which exhibits a change (such as a change in concentration, overall abundance, tertiary form or activity) in the transformation of a tissue from normal to diseased (such as neoplastic and/or inflammatory). Exemplary native fluorophores include tryptophan, reduced nicotinamide adenine dinucleotide (NADH), flavin adenine dinucleotide (FAD), elastin and collagen. In an embodiment, the target fluorophore is not a native fluorophore but is instead an exogenous administered substance which may be taken up by a tissue and/or cell in a disease state such as a cancerous process.

Tryptophan is a major source of fluorescence in cells. The fluorescence of a folded protein is a mixture of the fluorescence from individual aromatic residues. Most of the intrinsic fluorescence emissions of a folded protein are due to excitation of tryptophan residues, with some emissions due to tyrosine and phenylalanine; but disulfide bonds also have appreciable absorption in this wavelength range. Typically, tryptophan has a wavelength of maximum absorption of 280 nm and an emission peak ranging from 300 to 410 nm depending in the local environment. Hence, tryptophan fluorescence can be used as a diagnostic of the conformational state of a protein, as tryptophan fluorescence may be influenced by the proximity of other residues (i.e., nearby protonated groups such as Asp or Glu can cause quenching of Trp fluorescence). In an embodiment, tryptophan fluorescence can form part of a sensitive measurement of the conformational state of individual tryptophan residues. For example, if a protein containing a single tryptophan in its 'hydrophobic' core is denatured such as with increasing temperature, a red-shifted emission spectrum will appear. This is due to the exposure of the tryptophan to an aqueous environment as opposed to a hydrophobic protein interior. When illuminated, such as at 280 nm, a peak intensity of fluorescence from tryptophan at 330-340 nm is significantly greater in cancerous cells as compared to cells from the normal mucosa. The greater intensity of tryptophan fluorescence in dysplastic intestinal polyps can be correlated with increased tissue tryptophan content. Thus, the use of UV illumination enables this cellular signal to be incorporated into diagnostic images. In various embodiments, a technique involving images collected at multiple emission bands or time-resolved AF images may enable selective measurement of free proteins or free tryptophan and provide better diagnostic information than overall protein content. Tryptophan is a component of most cellular proteins, and thus, its fluorescence may provide a means to monitor intracellular protein content which may be altered significantly through the dysregulation of cellular growth processes associated with cancer. In various embodiments, the fluorescence response of tryptophan is much stronger than that of other native fluorophores such as reduced nicotinamide adenine dinucleotide (NADH) and flavin adenine dinucleotide (FAD), which permits faster image acquisition and reduced ultraviolet exposure.

Nicotinamide adenine dinucleotide, abbreviated $NAD^+$, is a coenzyme found in all living cells. The compound is a dinucleotide, since it consists of two nucleotides joined through their phosphate groups. One nucleotide contains an adenine base and the other nicotinamide. In metabolism, NAD is involved in redox reactions, carrying electrons from one reaction to another. The coenzyme is, therefore, found in two forms in cells: NAD is an oxidizing agent—it accepts electrons from other molecules and becomes reduced. This reaction forms NADH, which can then be used as a reducing agent to donate electrons. These electron transfer reactions are the main function of $NAD^+$. However, it is also used in other cellular processes, the most notable one being a substrate of enzymes that add or remove chemical groups from proteins, in posttranslational modifications. Because of the importance of these functions, the enzymes involved in NAD metabolism are targets for drug discovery.

Flavin adenine dinucleotide (FAD) (EC: 205-663-1) is a reduction-oxidation cofactor involved in several important reactions in metabolism. FAD can exist in two different redox states, which it converts between by accepting or donating electrons. The molecule consists of a riboflavin moiety (vitamin $B_2$) bound to the phosphate group of an ADP molecule. The flavin group is bound to ribitol, a sugar alcohol, by a carbon-nitrogen bond. The concentration of flavin adenine dinucleotide (FAD) may decrease with malignant transformation in metabolically active cancerous cells due in part to the anaerobic metabolism of glucose. An excitation wavelength of FAD is about 450 nm. Fluorescence from FAD is seen at 460 to 600 nm with maxima at about 550 nm.

Collagen fluorescence is a major fluorophore in the extracellular matrix. During early carcinogenesis, the basement membrane is degraded by matrix metalloproteinases with an attenuation of the intensity of fluorescence from the extracellular matrix in vicinity of the basement membrane. The fluorescence intensity from collagen can be further attenuated in neoplasms as substantial remodeling of the extracellular matrix occurs and the distance of its source to the epithelial surface increases. An excitation wavelength of collagen is about 320 nm. There is overlap between the fluorescence from NADH (400 to 550 nm with a peak at 450 nm) and collagen, however separation between the two can be obtained with excitation at 337 nm.

Elastin (UniProt P15502) is a protein in connective tissue that is elastic and allows many tissues in the body to resume their shape after stretching or contracting. The elastin gene encodes a protein that is one of the two components of elastic fibers (the other component is fibrillin). The encoded protein is rich in hydrophobic amino acids such as glycine and proline, which form mobile hydrophobic regions bounded by cros slinks between lysine residues.

Lipofuscin is the name given to finely granular yellow-brown pigment granule composed of lipid-containing residues of lysosomal digestion. It is considered to be one of the aging or "wear-and-tear" pigments, found in the liver, kidney, heart muscle, retina, adrenals, nerve cells, and ganglion cells. It is specifically arranged around the nucleus, and is a type of lipochrome. It is speculated that lipofuscin may be a product of the oxidation of unsaturated fatty acids, and may be symptomatic of membrane damage, or damage to mitochondria and lysosomes.

II. Ratiometric Formulae and Images

The excitation wavelengths and emission bands of the AF images may be chosen to target native fluorophores (such as tryptophan, collagen, NADH, FAD, porphyrins) whose concentrations and distributions may change with a disease state such as a cancerous process. Table 2 details six exemplary AF images of interest, named according to excitation wavelength, and their targeted tissue fluorophores. Excitation and emission spectra of several of these fluorophores may overlap, which may lead to marginal influence from non-targeted fluorophores in some images. Each of the AF images F280, F320, F340, F370, and F440 is formed by the subtraction of two different longpass-filtered images. For example, the 320-nm-excited AF image, F320, is formed by subtracting 410-nm longpass image from 375-nm longpass image to create an AF image associated largely with collagen. Likewise, the 280-nm excited fluorescence image is formed by subtracting 410 nm longpass image from 300 nm longpass image; the fluorescence image excited with 340 nm light is formed by subtracting a 500 nm long pass image from a 410 nm long pass image; and the fluorescence image excited with 440 nm light is formed by subtracting a 600 nm long pass image from a 500 nm long pass image.

TABLE 2

Autofluorescence images with names specifying excitation wavelength

| Name | Emission (nm) Target | Fluorophore (Other) |
|---|---|---|
| F280 | 300-410 | Tryptophan (Pyridoxine) |
| F320 | 375-410 | Collagen (Pyridoxine) |
| F340 | 410-500 | NADH (Collagen, Elastin) |
| F370 | 410-500 | Collagen (NADH, Elastin) |
| F400 | 600-655 | Porphyrins |
| F440 | 500-600 | FAD (Collagen) |

Visibility of lesions in fluorescence images may be increased by creating and applying formulaic ratio images. The ratios developed are not limited to simple division of two registered images (division applied pixel-by-pixel). Rather, a variety of novel ratio images are disclosed herein which may incorporate three or more images and may also include multiplication and/or addition. The formulaic computations are conducted based on a single or two and more images recorded at different optical configurations and named here A, B, C, D for illustration of four different images. Formulas based on simple ratios (1/A or A/B), three component ratios (A/B/C or A*B/C), ratios with additions such as 1/(A+B) or A/(B+C), or ratios with subtractions such as 1/(A−B) or A/(B−C) may be particularly useful as they can be computed quickly. In an embodiment, speed of calculation is part of a program/algorithm by which an appropriate ratiometric formula is chosen. Of particular usefulness are fluorescence images obtained at excitation/emission (nm) ranges as used in the following representative formulas: (250–300)/(300–400), 320/(350–450), (340–360)/(400–500), (400–450)/(500–600). Fluorescence recorded at longer wavelengths may also be particularly useful. The ranges listed above are sensitive to protein synthesis, protein content, extracellular proteolysis, cellular metabolism, as well as the structure and content of the extracellular matrix, including collagen and elastin contained therein. Particularly useful reflectance (nm) images include 350-400, 400-440, 450-500, 530-600, 600-700 and longer wavelengths as they are related to vascularity and proliferation, which typically change in disease processes such as cancer and inflammation.

A select group of specific formulaic ratio images with numerical R1, R2, R3, etc.) are presented in Table 3 using image names from Tables 1 and 2.

TABLE 3

Exemplary Ratiometric Formulas $$R1 = \frac{F280 * (F440 + F320)}{F440 * F320}$$

$$R2 = \frac{F280 + F340}{F440 + F320}$$

$$R3 = \frac{F280}{F440 + F320}$$

$$R4 = \frac{F280 * F340}{F440 * F320}$$

TABLE 3-continued

Exemplary Ratiometric Formulas $$R5 = \frac{F280}{F440 * F320}$$

$$R6 = \frac{1}{F440 + F320}$$

$$R7 = \frac{1}{F440 * F320}$$

$$R8 = \frac{F340}{F440 + F320}$$

$$R9 = \frac{F340}{F440 * F320}$$

$$R10 = \frac{1}{F440}$$

$$R11 = \frac{F280}{F440}$$

$$R12 = \frac{F280}{F320}$$

$$R13 = \frac{F280}{R555}$$

$$R14 = \frac{1}{R400}$$

$$R15 = \frac{F340}{F340 + F440}$$

$$R16 = \frac{R440}{R415}$$

$$R17 = \frac{R480}{R440}$$

$$R18 = \frac{1}{R440 * R400}$$

$$R19 = \frac{R440}{R370 * R480}$$

$$R20 = \frac{1}{R555}$$

$$R21 = \frac{F440red}{F440}$$

$$R22 = \frac{R555}{F440}$$

$$R23 = \frac{1}{F440red + F440}$$

$$R24 = \frac{1}{R555 + F440}$$

$$R25 = \frac{1}{R555 * F440}$$

$$R26 = \frac{1}{(F440)^2}$$

$$R27 = \frac{F340}{F440}$$

TABLE 3-continued

Exemplary Ratiometric Formulas $$R28 = \frac{F340}{F440 * F340uv}$$

$$R29 = \frac{F320blue}{F320}$$

$$R30 = \frac{R480}{R555}$$

One image name not detailed in Table 2 is F440red, which is an AF image excited at 440 nm with emission collected from 600-655 nm.

Ratio images may be formulated (automatically or manually) with the goal to make a lesion appear bright in comparison to surrounding normal tissue. As a general rule, to produce bright lesions. AF images expected to display increased lesion intensity (F280, F340) are placed in the numerator of ratios, while AF images expected to display decreased lesion intensity (F320, F440) are placed in the denominator. In some embodiments, simple mathematical inversions may be performed (R10, R20) to make dark lesions appear bright. In the ratios that include an addition operation, the average brightness of the individual images together contributes to a resulting ratio image. Images involved in an addition operation may be selected to possess similar average brightness or may be adjusted by a constant factor before ratio image calculation.

Absorption and scattering effects in tissue AF images may be corrected using a mathematical method to remove such distortions from tissue AF spectra measured with a fiber optic probe. The mathematical method may rely on collection of both reflectance and AF spectra, and may further involve other tissue optical properties. A simplified correction may be performed by dividing collected AF intensity at each emission wavelength by collected diffuse reflectance at the same wavelength. Similarly, an AF image may be divided by a cross-polarized reflectance image at the excitation wavelength, which may produce a ratio image corrected for variation in excitation-collection geometry and irregular tissue surface. In various embodiments, hypervascularity of the colonic neoplasm can be partly, if not completely, corrected by the dividing by a reflectance wavelength that is not readily absorbed by hemoglobin.

Based upon analysis of fluorescence/reflectance spectral images of cancerous lesions, select novel ratio images may be chosen (manually or automatically) with some formulae employing multiplication and/or addition and/or three or more images. Using quantitative, qualitative, and/or combined quantitative-qualitative measures, effective ratio images in terms of lesion contrast may be identified. The exceptional contrast levels of certain ratio images may translate into an increased detection of low contrast lesions such as flat lesions in the research and/or clinical setting. In various embodiments, this process of selecting high quality ratio images may be performed according to an algorithm which may be applied in an automated manner such as by using a microprocessor/computer. In one embodiment, the algorithm is specifically designed to choose a ratiometric formula which maximizes image contrast, such as calculated by a contrast metric such as Weber contrast (Equations 1a and 1b) and/or Equation 2. Ratio images may be combined (manually or automatically such as using an algorithm) to further distinguish lesions. For example, as discussed in Example 7, fluorescence ratio images A/B where A=Fluorescence at 340 nm excitation (F340) and B=Fluorescence at 440 nm excitation (F440) combined with ratio C/D where C=Reflected light at 480 nm and D at 555 nm produced the largest number of formulaic images with exceptional contrast.

It should be appreciated that the methods for allowing users to perform ratiometric imaging may also include displaying images and/or underlying data in real-time or near real-time within a module, portal, or other display environment. The display step may occur locally or remotely relative to the location of the execution of the other steps in the method. For example, as mentioned above, ratiometric images may be pushed to an end user or pulled by an end user. As such, the end user may access the ratiometric imaging data at any location with various types of devices.

Each of the steps described above for performing ratiometric imaging may be automated, although one or more of the steps may not be automatic or automated. The automation of the steps eliminates the human error accidentally failing to set up or perform a mathematical or other step correctly (e.g., miscalculation or mis-entry). For example, the generation and/or testing (e.g., contrast testing) of formulaic ratios may be automated. This may allow a user to avoid the step of selecting and/or comparing specific formulas for maximizing contrast. In one embodiment, automation of formula generation involves use of a random or semi-random formula generator which may select from a set of image types. In one embodiment, a user inputs a fixed set of image types into the computer which generates candidate formulae. The calculation steps according to the formulas may also be automated, and may be performed by the same or a different microprocessor from the one performing the selecting/comparing step. As described below, the method may be implemented into a computer-readable storage medium and be carried out with the aid of a computer.

A computer-readable storage medium, such as a non-volatile storage medium, may comprise any of the steps described above. The computer program may be generated in any software language or framework such as C#, COBOL, C++, Java, Microsoft® .NET Framework or the like.

The computer-readable medium for performing the embodiments of the present disclosure may include computer-readable program code portions, such as a series of computer instructions, embodied in the computer-readable medium. It should be understood that the computer-readable program code portions may include separate executable portions for performing distinct functions to accomplish embodiments of the present disclosure. Additionally, or alternatively, one or more of the computer-readable program portions may include one or more executable portions for performing more than one function to thereby accomplish embodiments of the process of the present disclosure.

In conjunction with the computer-readable storage medium, a computer that includes a processor, such as a programmable-variety processor responsive to software instructions, a hardwired state machine, or a combination of these may be used to carry out the methods disclosed herein. Such computers may also include memory, which in conjunction with the processor is used to process data and store information. Such memory can include one or more types of solid state memory, magnetic memory, or optical memory, just to name a few. By way of non-limiting example, the memory can include solid state electronic random access memory (RAM); sequential access memory (SAM), such as first-in, first-out (FIFO) variety or last-in, first-out (LIFO)

variety; programmable read only memory (PROM); electronically programmable read only memory (EPROM); or electronically erasable programmable read only memory (EEPROM); an optical disc memory (such as a DVD or CD-ROM); a magnetically encoded hard disc, floppy disc, tape, or cartridge media; or a combination of these memory types. In addition, the memory may be volatile, nonvolatile, or a hybrid combination of volatile and non-volatile varieties. The memory may include removable memory, such as, for example, memory in the form of a non-volatile electronic memory unit; an optical memory disk (such as a DVD or CD ROM); a magnetically encoded hard disk, floppy disk, tape, or cartridge media; or a combination of these or other removable memory types.

The computers described above may also include a display upon which information may be displayed in a manner perceptible to the user, such as, for example, a computer monitor, cathode ray tube, liquid crystal display, light emitting diode display, touchpad or touchscreen display, and/or other means known in the art for emitting a visually perceptible output. Such computers may also include one or more data entry, such as, for example, a keyboard, keypad, pointing device, mouse, touchpad, touchscreen, microphone, and/or other data entry means known in the art. Each computer also may comprise an audio display means such as one or more loudspeakers and/or other means known in the art for emitting an audibly perceptible output.

Quantitative Image Analysis

Various metrics may be employed to quantify lesion visibility and thus compare the effectiveness of various ratio and non-ratio images. A first metric (Equations 1a & 1b) is based on the well-known Weber contrast which takes the form $(I_A-I_B)/I_B$. A second metric is a novel optimized metric (Equation 2). In equations 1a & 1b, $I_{Lesion}$ and $I_{Normal}$ are the mean pixel intensities inside the respective ROIs of a specimen image. Similarly, in equation 2, $I_{Lesion,75\%}$ and $I_{Normal,75\%}$ are the $75^{th}$ percentile level pixel intensities inside respective Ms of the specimen image. Furthermore, $\sigma_{L,N}$ is the pooled standard deviation as calculated from the individual standard deviations, $\sigma_L$ and $\sigma_N$, of the pixel intensities inside the image lesion and normal ROIs.

$$C_w = \frac{I_{Lesion} - I_{Normal}}{I_{Normal}} \quad (1a)$$

$$C_{w\_I} = \frac{I_{Normal} - I_{Lesion}}{I_{Lesion}} \quad (1b)$$

$$C_{Opt} = \frac{|I_{Lesion,75\%} - I_{Normal,75\%}|}{\sigma_{L,N}} \quad (2)$$

where $$\sigma_{L,N} = \sqrt{\frac{(\sigma_L^2 + \sigma_N^2)}{2}}$$

The optimized contrast metric of Equation 2 disclosed herein was developed in response to observations that the Weber contrast can bias towards formulaic ratio images of the form 1/(A*B) and against ratio images like A/(A+B) or A/B. In the optimized contrast metric it is important to account for the standard deviation, or spread, of the ROI pixel intensities. While ratios of the form 1/(A*B) have a tendency to magnify $I_{Lesion}-I_{Normal}$ (numerator of equation 1a), they also tend to increase the spread of pixel intensities, potentially negating this improvement in displayed images. Inspection of pixel intensity histograms from ratio images also showed highly asymmetric distributions for which the mean may not be a very reliable statistic.

Image Scaling and Analysis

Ratio image calculation can produce a wide range of image intensity values and a variety of distributions, making consistent display a nontrivial task. A variety of methods may be used to scale image data for display, such as in grayscale on a monitor. In the "fixed" scaling method, intensities from a large number of images of the same type are observed collectively and a suitable minimum and maximum intensity level chosen to set the low and high ends of the display range. The scaling is "fixed" because every image of the same type is scaled identically. Fixed scaling is appropriate for the basic AF and reflectance images because the overall variation in intensity values may be low, and the fixed scaling of calibrated data allowed quantitative comparison of measurements from specimen to specimen. A second method, "autoscaling," is an adaptive method in which new minimum and maximum intensity levels are chosen for each individual image. This method can provide each image with substantially the same number of completely white and completely black pixels and may alternately be called saturation scaling. A third method, "histogram equalization" is an adaptive method in which not only are appropriate maximum and minimum intensity levels determined, but nonlinear scaling adapts an image intensity distribution to a preselected shape. The result is a more vibrant image which is also less quantitative due to the nonlinear scaling. In any such scaling methods, a given percentage (e.g., 1% of intensities) may be intentionally saturated at both the high and low ends to achieve a preferred contrast with little loss of information.

Figure 4:
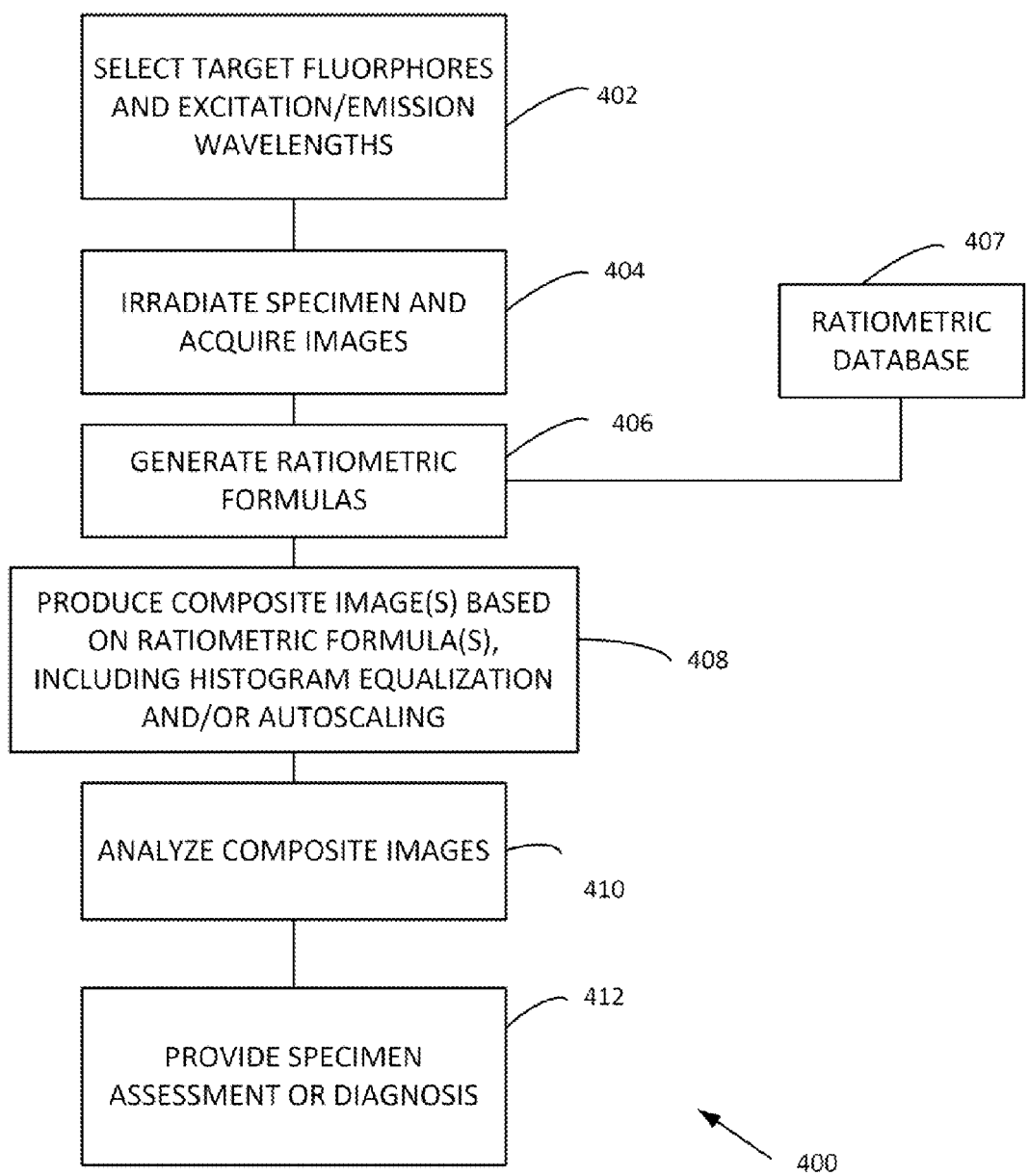
FIG. 4 is a flowchart showing a representative method of selecting and producing ratiometric images for the diagnosis of a disease state.

Referring to FIG. 4, a representative method 400 includes selecting target fluorophores, and emission and excitation wavelengths at 402. At 404, a specimen is interrogated based on the selected wavelengths and fluorophores, and associated specimen images are acquired. At 406, one or more ratiometric formulas are generated for image processing, or formulas are retrieved from a formula database 407. At 408, composite images are produced by processing the acquired images based on one or more ratiometric formulas. At 412, a specimen assessment is provided based on the analyzed composite images. In some examples, analysis is based on direct image viewing, but computer-based image evaluation can also be used.

Although methods and materials similar or equivalent to those described herein can be used in the practice or testing of the present disclosure, suitable methods and materials are described below. All publications, patent applications, patents, GENBANK® Accession numbers and other references mentioned herein are incorporated by reference in their entirety. In case of conflict, the present specification, including explanations of terms, will control. In addition, the materials, methods, and examples are illustrative only and not intended to be limiting.

The following examples are provided to illustrate certain particular features and/or embodiments. These examples should not be construed to limit the disclosure to the particular features or embodiments described.

EXAMPLES

Example 1

Application to a First Set of Specimens—Methods and Materials

Examples 1-7 detail results obtained from application of the disclosed methods and systems to a first set of fresh human colon surgical specimens. 21 of 30 specimens in the set involved adenocarcinoma and 9 of the 30 involved adenomas. The low number of adenomas acquired reflects the fact that adenomas are precursor lesions removed by surgery only when colonoscopic removal is not feasible. Quantitative comparison of specimen AF intensities was desired, and to reduce influence of factors not being studied, nine specimens were omitted from the analysis.

Colon specimens were obtained fresh from surgery and studied in a separate room in the same building. Specimens were positioned with the luminal surface facing up, and the mucosa was rinsed with saline to remove any blood or stool. Imaging was performed in a darkened room thirty to sixty minutes after excision. Images were composed to include the edge of the lesion allowing comparison of the lesion and surrounding normal mucosa in a single photograph. Reference color images of specimens were collected with a standard digital SLR camera. Histopathology of each specimen was collected and used as the gold standard for diagnosis. AF images were produced using various excitation wavelengths from 280 to 440 nm. Formulaic ratio imaging was used to combine spectral images, resulting in increased contrast which caused neoplasms to appear bright compared to normal tissue.

In preparation for quantitative analysis, raw images were processed using MATLAB mathematical analysis tools (The MathWorks, Natick, Mass.). Dark current and room light in the raw images were compensated by subtracting corresponding dark frames (illumination blocked with shutter). Hat fielding was performed through division by a normalized image of a white standard. Source power variation was compensated through division by single correction factors representing relative power readings on date of imaging. Integration times were also corrected as appropriate using a multiplicative factor.

Figure 5:
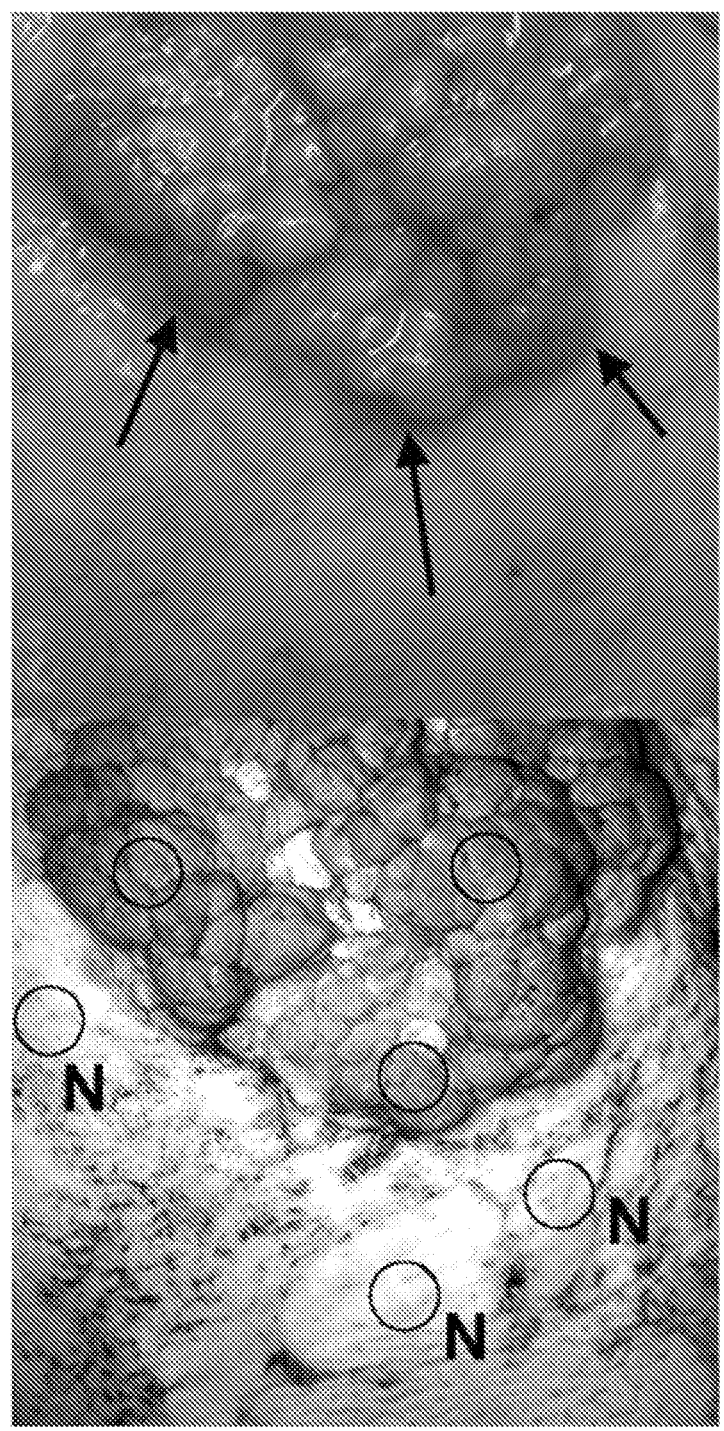
FIG. 5 is a pair of images showing regions of interest (ROIs) assigned in the vicinity of an adenocarcinoma lesion. The top image is a reference image with arrows pointing to the raised edge of the adenocarcinoma. The bottom image is an F280 image with three circular ROIs labelled with an N to designate normal tissue and three unmarked ROIs representing the lesion.

Circular regions of interest (ROIs) were selected manually in each specimen image (using MATLAB) and saved to facilitate quantitative analysis of intensity difference between lesion and normal regions. This task was performed with input from a physician experienced in colonoscopy. For each image, one or more ROIs were selected to represent the lesion in the image and those pixel positions assigned to a lesion pool. Similarly, one or more ROIs were then selected from the most normal appearing tissue in the image and those pixels assigned to a normal pool. Lesion and normal ROIs were manually traced over F280 images while viewing a standard color reflectance image as a reference. The examiner was blind to any of the other images. Example ROIs for a particular specimen image are shown in FIG. 5. ROIs for each specimen image were saved and later applied identically to all AF images, reflectance images, and ratio images. Often two or more fields of view had been imaged showing different portions of one specimen. In this case a single image set involving just one field of view was chosen for analysis of each specimen. In quantifying lesion contrast, two versions of the Weber metric (Equations 1a & 1b) were needed to compare two different types of images. Original intensity images (Tables 1 & 2) consistently displayed reduced lesion intensity ($I_{Lesion} < I_{Normal}$), regardless of the image wavelength and its AF or reflectance nature. In formulaic ratio images (Table 3), however, lesions by design appeared brighter than the surrounding normal tissue ($I_{Lesion} > I_{Normal}$). Therefore, equation 1a was used in formulaic ratio images, and equation 1b was used in original intensity images.

Example 2

Contrast Results for Original Intensity Images—Adenomas and Adenocarcinomas

Figure 6:
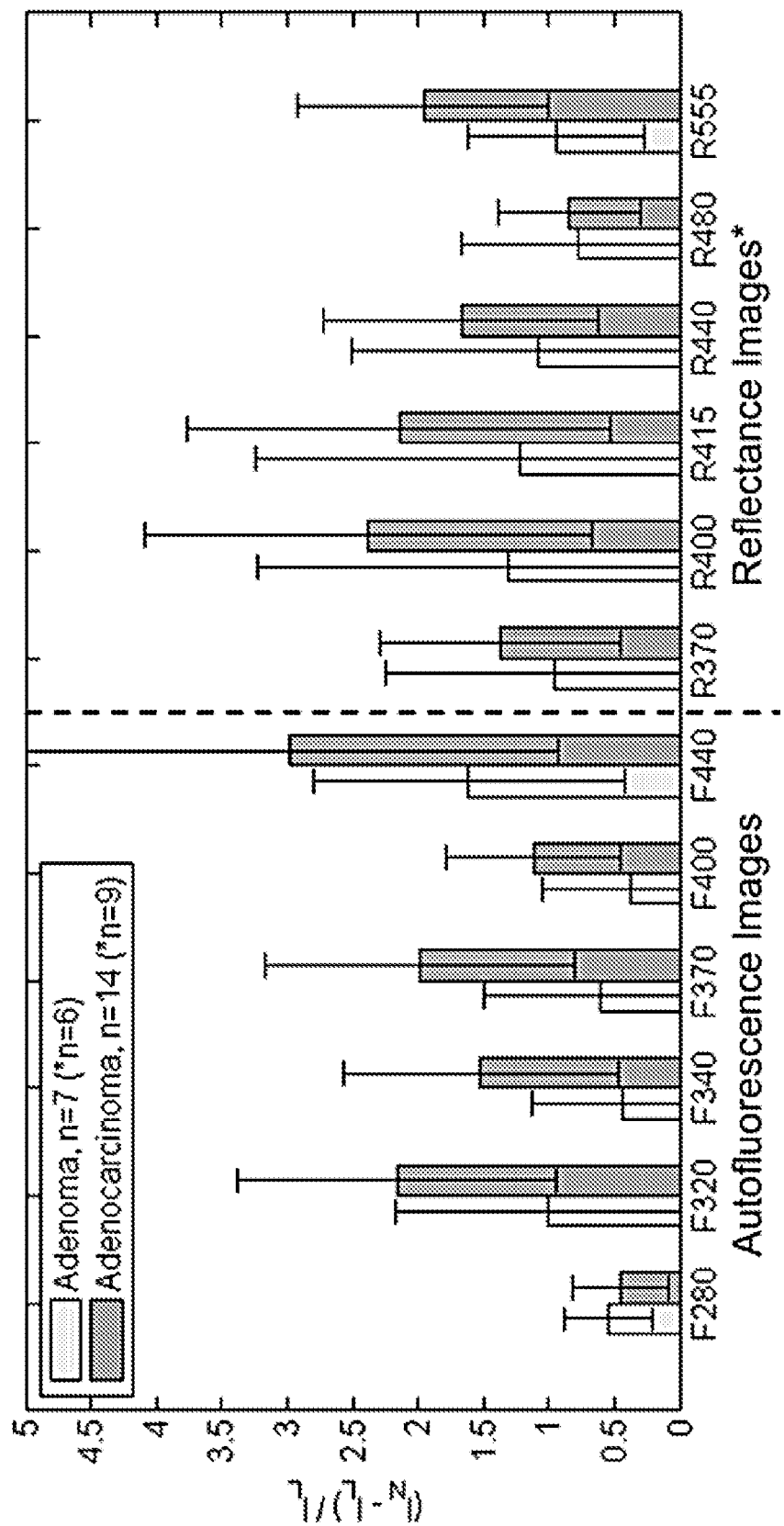
FIG. 6 is a plot showing contrast results for adenomas and adenocarcinomas (includes low-contrast and non-low-contrast lesions) using various single wavelength, non-ratiometric auto-fluorescence and reflectance images.

FIG. 6 shows mean lesion contrast in AF and reflectance original intensity images with specimens stratified by histology (adenomas (n=7) and adenocarcinomas (n=14)) for all lesion types (including both normal lesions and LCLs). Reflectance images were available only for the last 6 adenomas and 9 adenocarcinomas. This plot specifies the mean and standard deviation of the Weber contrasts calculated for each image type. Adenocarcinomas were visualized more readily than adenomas as evidenced by their higher contrast values.

The positive contrast values indicate that for all image types the lesion produced lower image intensities than the surrounding normal mucosa. F440 produced the highest mean contrast in both the adenomas and adenocarcinomas studied. However, considering only adenocarcinomas, F440 displayed no statistically significant increase in contrast over image types R400, R415, R555, F320, and F370 (T-test, $p > 0.05$). The increase was yet less significant in the adenoma group with only F280, F340, and F400 judged lower contrast than F440 by T-test ($p < 0.05$). F280 was unique in its production of very low contrast for both adenoma and adenocarcinoma groups. The mean contrast of adenomas in the F340 and F400 images was notably low and even negative for some specimens as can be inferred by the error bars. It should also be noted that the majority of lesions in the adenocarcinoma group were well-established masses with increased vascularity. The influence of hemoglobin in the contrast of the narrowband reflectance images is evident in the right side of FIG. 6, because the contrast of reflectance images versus wavelength resembles the absorption spectrum of hemoglobin, which has primary peaks between 400 and 440 nm and a local maximum near 550 nm.

From both quantitative contrast information and visual review of images, a trend was observed that adenomas are more difficult to identify than adenocarcinomas in both AF and reflectance images. Adenocarcinomas tended to appear more vascular than the surrounding tissue, and increased hemoglobin concentration may modulate contrast with the least affected images being R480 and F280.

Example 3

Figure 7:
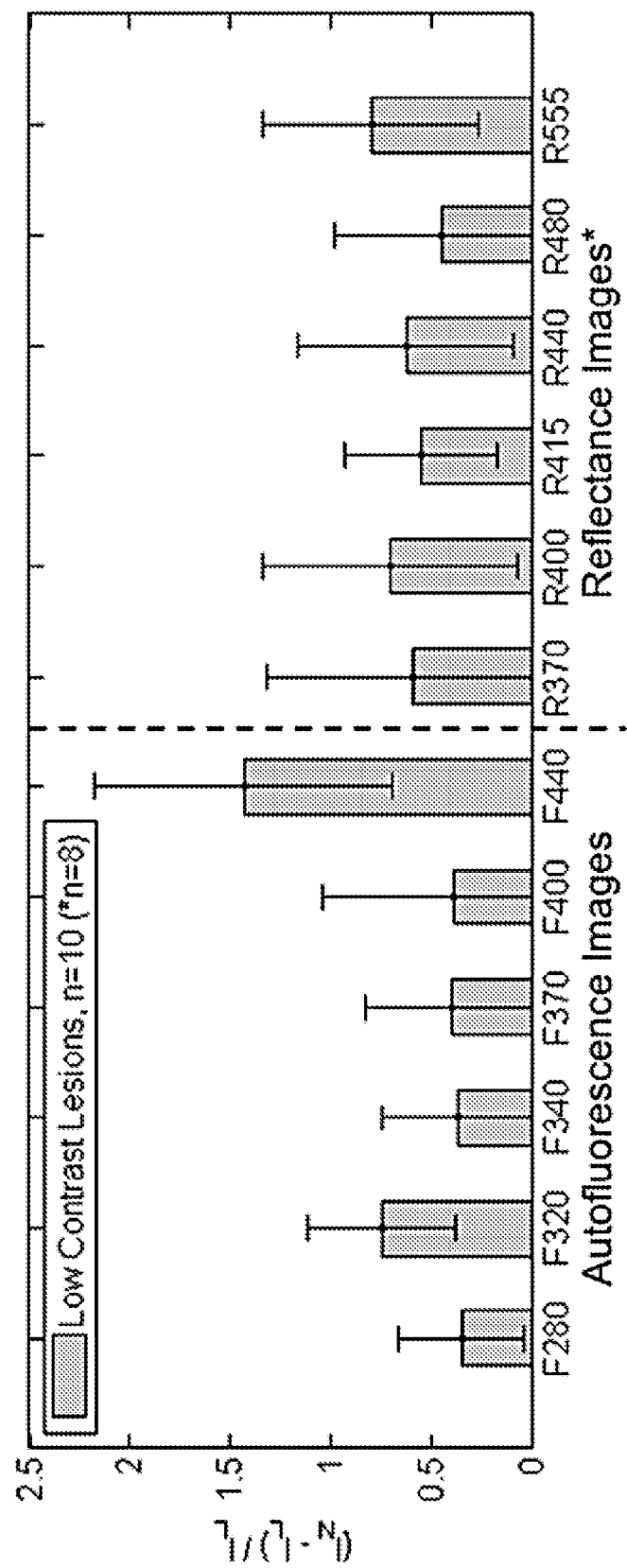
FIG. 7 is a plot showing contrast results in adenomas and adenocarcinoma low-contrast lesions (LCLs) using various single wavelength, non-ratiometric auto-fluorescence and reflectance images.

Original Intensity Image Contrast Results in Low Contrast Lesions (LCLs)—Adenomas and Adenocarcinomas This example provides single fluorescence image contrast results for a subgroup of LCLs including six adenomas and four adenocarcinomas. As shown in FIG. 7, AF image F440 performed best in identification of LCLs. The increase in contrast of F440 over all the other image types plotted was confirmed in T-test comparisons ($p < 0.05$).

Although F440 was the most useful of the original intensity images tested, roughly half of the LCLs could not be well visualized directly with F440 fluorescence intensity. There was also interference from blood and geometrical features (folds) which appeared dark and could reduce specificity.

Example 4

Formulaic Ratio (FR) Image Contrast Results in the LCLs—Weber Contrast and Novel Optimized Contrast Metrics Formulaic ratio images were sought to gain high visualization of additional LCLs. Over thirty formulae were attempted and evaluated. Weber contrast, as expressed in Equation 1a, was initially used in conjunction with visual analysis to compare performance of the ratio images. A novel, improved contrast metric was sought when results of the first metric were found in some cases to disagree with visually-assessed scores of the formulaic ratio images. The optimized metric (Equation 2) favors bright areas within the regions of interest and diminishes in response to increased intensity variance within the regions of interest. The performance of formulaic ratio images as measured by the optimized contrast metric and Weber contrast is illustrated in FIG. 8, where the calculated contrast is plotted against the visual contrast scores. A higher correlation with visual contrast scores was achieved with the optimized metric.

Nine of the highest performing ratio images were selected for further evaluation. Narrowing the pool was achieved by first grouping the ratio images by visual similarity. Six such groups were identified as well as four ratios with performance seemingly superior to the others. Equation 2 was then used to calculate lesion contrast for all ratio images and all specimens. The mean contrast metric score and standard deviation of each formulaic ratio image type were compared by stratifying adenocarcinoma, adenoma, and low contrast lesions. Formulaic ratio images with high performance in one or more of these categories were chosen for careful visual analysis. It was furthermore desired to retain formulae from each of the six groups of similar visual impression. This approach resulted in nine formulaic ratio images with very high diagnostic potential (Table 4).

TABLE 4

Select Ratiometric Imaging Formulae $$R7 = \frac{1}{F440 * F320}$$

$$R10 = \frac{1}{F440}$$

$$R15 = \frac{F340}{F340 + F440}$$

$$R20 = \frac{1}{R555}$$

$$R23 = \frac{1}{F440red + F440}$$

$$R24 = \frac{1}{R555 + F440}$$

$$R25 = \frac{1}{R555 * F440}$$

$$R27 = \frac{F340}{F440}$$

$$R30 = \frac{R480}{R555}$$

Example 5

Effects of Auto-Scaling and Histogram Equalization on FR Images

The appropriate method of scaling each formulaic ratio image was determined by observing visual results on images of all specimens. Examples of the effects of autoscaling and histogram equalization are illustrated in FIGS. 9A-9F. The better scaling choice correlated with the form of the ratio used to calculate the image. Ratio images such as R27 and R30, having the form A/B and small ranges of intensities, were displayed effectively with autoscaling. Autoscaling was slightly less effective for ratios of the form 1/A and 1/(A+B) but still the preferred choice. For ratio image R7 of the form 1/(A*B), histogram equalization was the preferred scaling method for display. When it was autoscaled, this ratio image frequently became dark because a small but substantial percentage of pixel intensities were considerably higher than any other pixels in the image. For ratio image R15, which has the form A/(A+B), histogram equalization was preferred because autoscaling produced a washed out appearance.

Example 6

Performance of Nine Selected Ratios on Normal and Low Contrast Lesions

Figure 10:
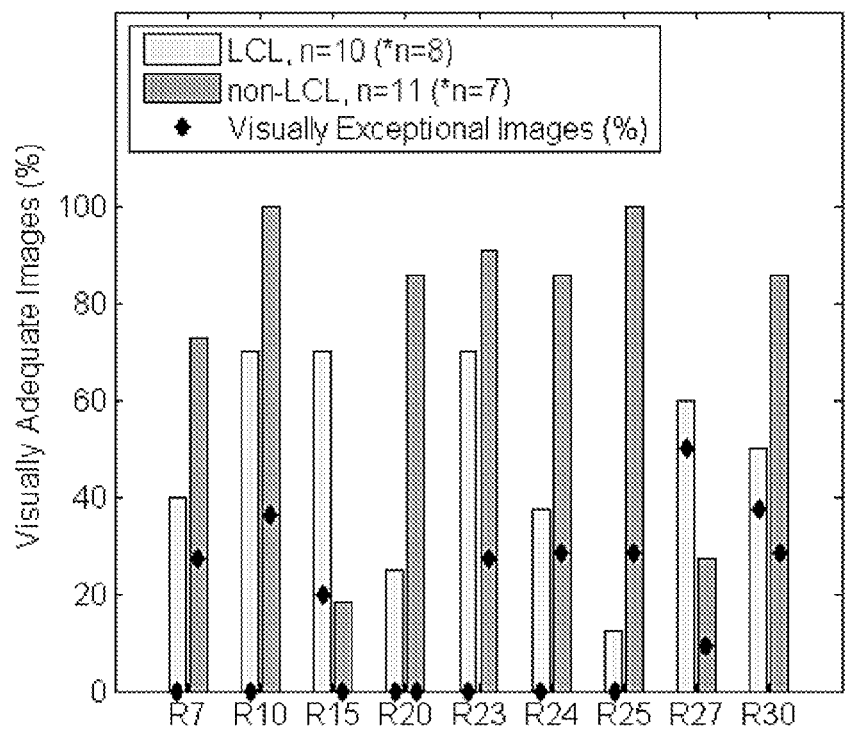
FIG. 10 is a bar chart showing the performance of formulaic ratio images produced by the exemplary ratiometric imaging system based on visual assessment. Bars represent the percentage of specimen images for which a majority of observers (at least 4 of 7) deemed the image "adequate" for lesion identification. Diamonds represent the percentage of specimen images for which at least 3 of 7 observers deemed the image "exception". Results are stratified by low contrast lesion (LCL) status of specimens.

Visual analysis of the nine selected ratio images (Table 4) was conducted by tiling the nine images of a single specimen on a large display, recording visual scores, and repeating the process for all specimens. The identity of each tiled ratio image was concealed from the observers. Results were stratified by LCLs versus non-LCLs and compiled in FIG. 10 as percentages of specimens imaged for which a majority of observers deemed the image "adequate" for lesion identification. As narrowband reflectance imaging was not available for the first six specimens, ratio images R20, R24, R25, and R30 were not available for six out of twenty-one specimens. However, this is accounted for by plotting results as percentages of specimens imaged. The data demonstrate that image R10 (1/F440), regardless of specimen group, was never exceeded in its ability to produce adequate contrast. Image R23 [1/(F440red+F440)] was nearly identical to R10 in appearance and visual performance. Ratio image R27 (F340/F440) showed a propensity for exceptional depiction of LCLs as well as adequate performance on nearly the same percentage of lesions as R10. R30 (R480/R555) produced many exceptional images in both lesion subgroups but produced less adequate images when compared to R10. A second stratification (adenoma versus adenocarcinoma, not shown) produced highly similar results due to the majority of the LCLs being adenomas and the majority of non-LCLs being adenocarcinomas.

Figure 11:
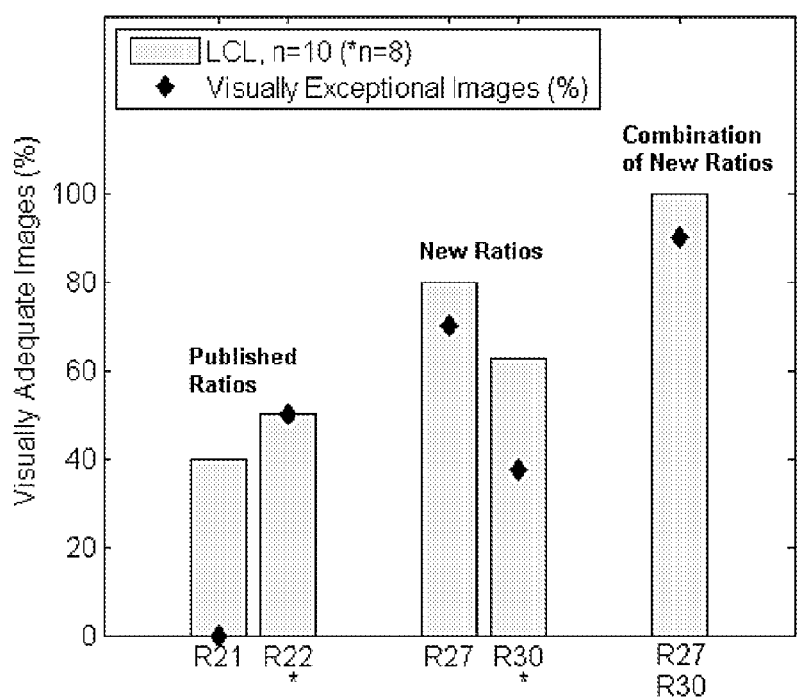
FIG. 11 is a bar graph comparing visually-assessed performance of existing technologies to the performance of the exemplary ratiometric imaging system disclosed herein using the novel ratio image R27: 340/440. Ratio image R21=F440red/F440 approximates the red/green ratio used for polyp discrimination by LIFE-GI. Image R22=R555/F440 approximates the G/R ratio used by the AFI system. Bars represent the percentage of low contrast lesion images for which the ratio image was deemed "adequate" for lesion identification by at least 4 of 8 observers. Diamonds represent the percentage of specimen images for which the ratio image was deemed "exceptional" by 3 or more of 8 observers. The rightmost bar indicates the performance achievable using R27 and R30 in parallel, such as by combining ratio images.

In order to compare the most successful ratio images to commercial AF endoscope technology, a second visual analysis was performed using the same procedure as the first but including ratio images R21 simulating the LIFE-GI system and R22 simulating the AFI system. To reduce potential bias, the eight persons participating in the second visual analysis were also blinded to the identity of the images being evaluated. Results are presented in FIG. 11. An advantage is seen for R27 in percentage of LCLs visualized both exceptionally and adequately. The data also demonstrate that performance can be further improved using R27 and R30 in parallel due to the complementary ability of the two ratio image types.

Ratio images simulating color contrasts of the LIFE-GI and AFI colonoscope systems also displayed considerably less contrast than the newly discovered ratio R27 for a low-contrast large flat polyp (tubulovillous adenoma) in a proximal colon specimen.

Example 7

Combining Multiple Ratio Images

Figure 12:
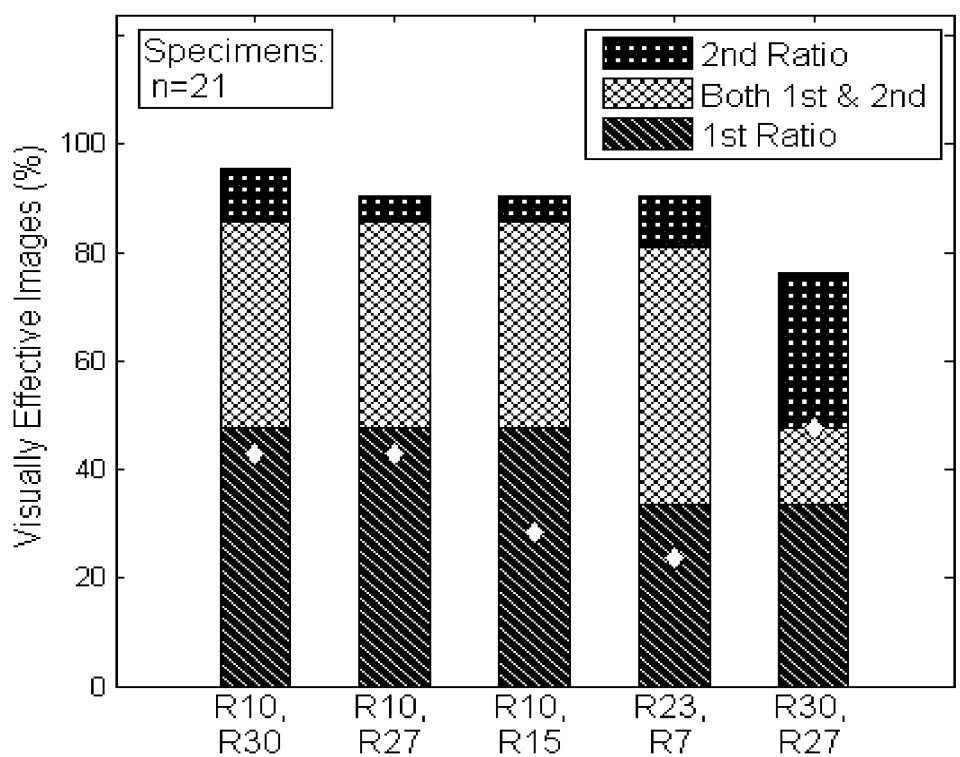
FIG. 12 is a stacked bar graph showing visually-assessed combined performance of pairs of formulated ratio images. Overall bar height represents the percentage of specimen images for which at least one of the two listed ratio images was deemed "adequate" for lesion identification by a majority of observers (at least 4 of 7). The relative size of shaded bar segments indicates the unique contribution of each ratio image, as well as the contribution that is common to both ratios. Diamonds represent the percentage of specimen images for which at least one of two ratio images was deemed "exceptional" by 3 or more of 7 observers. R10 and R30 are the most effective pair for this dataset.

A subset of formulaic ratio images were identified such that at least one member of the subset would produce high lesion contrast for all of the specimens imaged (LCLs and normal contrast). Using the same criteria as FIG. 10 to determine if specimen images were "adequate" and "exceptional", useful combinations of any two of the nine ratios were visually assessed. The results are shown in a stacked bar chart (FIG. 12) such that the unique contribution of each ratio image can be seen as well as the overlap. The combination of R10 and R30 allowed visually adequate contrast for the most specimens (20 of 21). Eight other combinations of two ratios achieved 19 of 21; however the three combinations shown are those that would achieve 20 of 21 if voting threshold (number of observers required to judge an image as visually adequate) were lowered from 4 of 7 to 3 of 7. The R30 and R27 combination resulted in the highest number of exceptional contrast images. Additionally, the R30 ratio was not available for the first six specimens and potentially could have achieved a score as high as 19 of 21 if it had been available.

Example 8

Targeting Tryptophan, Flavin Adenine Dinucleotide (FAD) and Collagen

This example details a separate set of results obtained using fresh surgical specimens of the colon containing normal mucosa, polypoid and flat adenomas and adenocarcinoma. A total of 24 patients had lesions identified in previous colonoscopy and were taken to the operating room for colonic resection. Of the 24 patients, 8 were excluded for device malfunction, ulcerative colitis, previous chemotherapy and radiation or exudates present. The remaining lesions were then grouped into distal- (splenic flexure to the rectum) colorectal lesions, proximal- (cecum to the hepatic flexure) colorectal lesions, or adenomatous polyps. After exclusions as described above, there were 4 patients with distal-lesions, 9 patients with proximal-lesions and 3 patients with adenomatous polyps. One patient in the adenomatous polyp category had a total of 6 separate lesions. A total of 8 lesions were imaged. Lastly, a patient with a serrated adenomatous polyp was included.

Specimens were collected following resection, transported to the imaging laboratory and irrigated with normal saline to remove stool and/or blood. All specimens were imaged 30-45 minutes after resection using a prototype wide-field spectral imager capable of illumination from 260 to 650 nm and detection from 340 to 650 nm and constructed to measure tissue autofluorescence and reflectance over a 40-mm square field-of-view. Each specimen was rinsed with saline and a color image was taken of each specimen with a digital camera (Nikon D100, Nikon Inc., Melville, N.Y.). Once the reflectance and autofluorescence images had been captured, they were saved as 16 bit TIFF files and loaded into Matlab as 512×512 image files (Mathworks, Natick, Mass., USA) for production of ratio images. For a ratio image of the form (A/B), the intensity value associated with each individual pixel in the 512×512 pixel image A was divided by the intensity value of the corresponding pixel in image B. If a ratio involved multiplication, the intensities were multiplied. The resulting intensity value from the mathematical operation was then mapped to the respective pixel, and after all pixels had been processed, the final ratio image was created.

An exemplary high contrast ratiometric image is achieved using fluorescence images targeting tryptophan, FAD and collagen. In non-ratiometric tryptophan autofluorescence images of the human colon, the intensity of fluorescence in neoplasms may be attenuated due to scattering and absorption by hemoglobin. However, when divided by the product of collagen and FAD fluorescence, neoplasms are displayed as bright lesions with high contrast that are superior to the contrast obtained with existing autofluorescence systems. The image intensity of a fluorescence image targeting tryptophan was divided pixel by pixel, by the intensities of images targeting FAD and collagen to produce a formulaic ratio (FR) image.

Figure 13A:
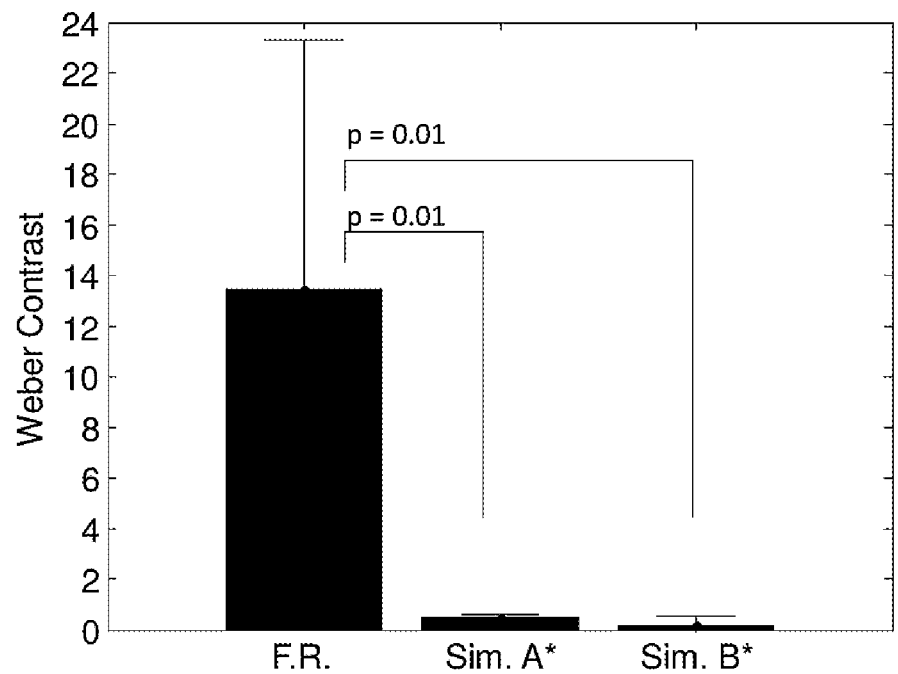
FIGS. 13A and 13B are bar graphs showing contrast levels achieved for adenocarcinomas and adenomas, respectively, by existing imaging systems (Sim A=AFI system and Sim B=OL system) and by the exemplary ratiometric imaging system disclosed herein using novel formulaic ratio images.
Figure 13B:
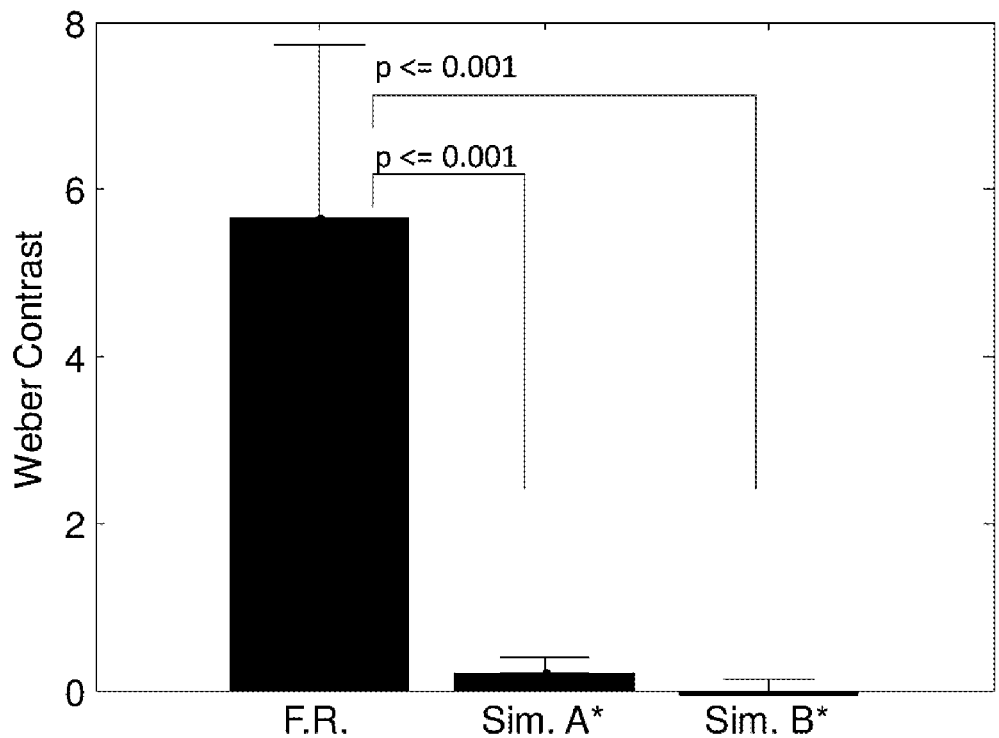

This formulaic ratio (FR) image consistently produced greater contrast for all classes and regions of lesions than images producible by AFI and OL systems (Sim A and Sim B). Formulaic ratio images as disclosed herein may be compared to existing technology as represented by ratio images approximating the color contrasts of two different commercial AF colonoscopes. Ratio image R21 (=F440red/F440) is modeled after a red/green ratio (ratio of red AF to green AF) approximating color in the LIFE-GI system. Ratio image R22 (=R555/F440) simulates a G/R ratio (ratio of green AF to green reflectance) approximating color tone in the AFI system. Intensity differences in grayscale images R21 and R22 estimate the color differences used in each system's pseudocolor display images to identify lesions. FIG. 13A quantifies the FR image intensities of adenocarcinomas in comparison to the normal mucosa using Weber contrast. The mean Weber contrast for the FR images of adenocarcinomas was 13.5±9.8. The FR images contain far greater contrast than the corresponding mean Weber contrasts of Sim A and Sim B of the same lesions: 0.47±0.13 (p=0.01) and 0.19±0.35 (p=0.01, t-test) respectively. FIG. 13A shows that, using the ratiometric analysis disclosed herein, Weber contrast of adenocarcinomas was 10-times higher than the contrast produced in the simulated AFI and OL images. FIG. 13B depicts the Weber contrast of all adenomas compared to the normal mucosa: 5.6±2.1. The FR images produced far superior contrast than Sim A 0.20±0.19 (p<0.001) and Sim B −0.05±0.18 (p<0.001) by t-test. FR images produced a mean Weber contrast of 5.6±2.1 for adenomas and 13.5±9.8 for adenocarcinomas, which was about 3 times higher (p<0.08; t-test). In differentiating between adenomas and adenocarcinomas, the formulaic images show a 5-fold to 10-fold increase in contrast of lesions compared to the AFI and OL systems.

FIG. 14 organizes the data into proximal- and distal-adenocarcinomas. The mean Weber contrast for FR images of the distal lesions and proximal lesions were 23.3±4.0 and 9.6±8.5 respectively. The Weber contrast for distal lesions was 2.4 times that of proximal lesions. The Weber contrast of the formulaic images was 5-fold and 20-fold higher for both proximal and distal lesions than AFI and OL, respectively. While the comparisons are made in the grayscale mode and not using pseudocolor, it will be recognized that pseudocolor can also be incorporated in FR images.

We claim:

1. A method for visualizing a lesion in a specimen, comprising:
applying a plurality of excitation signals to the lesion in the specimen, wherein the excitation signals comprise optical radiation having wavelengths between 200 nm to 700 nm, and wherein each of the plurality of excitation signals targets a different native fluorophore or chromophore;
producing images from autofluorescence emitted from at least one native fluorophore in the specimen in response to each of the plurality of excitation signals;
producing images from reflectance from the specimen;
producing a ratio reflectance image from the images produced from reflectance, using a reflectance band measured in the range of 450 to 500 nm and a reflectance band measured in the range of 530 to 600 nm; and
producing a ratio autofluorescence image based on the images produced from autofluorescence, using 1/([F400 nm to F450 nm]*F320 nm); 1/(F400 nm to F450 nm); (F340 nm to F360 nm)/((F340 nm to F360 nm)+(F400 nm to F450 nm)); 1/((F400 nm to F450 nm)+(F400 nm to F450 nm)); ((F250 nm to F300 nm)*(F340 nm to F360 nm))/(F400 nm to F450 nm), or (F340 nm to F360 nm)/(F400 nm to F450 nm),
thereby visualizing the lesion in the specimen.

2. The method of claim 1, wherein the emitted autofluorescence and the reflectance are optical radiation in a wavelength range of 300 nm to 700 nm.

3. The method of claim 1, further comprising maximizing image contrast of the ratio reflectance image or the ratio autofluorescence image according to the equation:

$$C_{Opt} = \frac{|I_{Lesion,75\%} - I_{Normal,75\%}|}{\sigma_{L,N}}$$

wherein $$\sigma_{L,N} = \sqrt{\frac{(\sigma_L^2 + \sigma_N^2)}{2}}.$$

4. The method of claim 1, wherein the excitation signals comprise optical radiation having wavelengths between about 280 nm and about 440 nm or between 400 nm and 700 nm.

5. The method of claim 1, wherein the native fluorophore comprises tryptophan, collagen, flavin adenine dinucleotide (FAD), lipofuscin or nicotinamide adenine dinucleotide (NADH).

6. The method of claim 1, wherein the plurality of excitation signals have a wavelength of about 280 nm, 340 nm, 440 nm.

7. The method of claim 1, wherein the lesion is a pre-cancerous or cancerous lesion.

8. The method of claim 1, further comprising combining the ratio reflectance image and the ratio autofluorescence image to form a composite ratio.

9. The method of claim 1, wherein at least three excitation signals are applied to the specimen, wherein each excitation signal targets a different native fluorophore.

10. The method of claim 1, wherein the native fluorophore comprises tryptophan, collagen, NADH, and FAD.

11. The method of claim 1, wherein producing the ratio reflectance image comprises using ratiometric formula R480/R555 or 1/R555, and wherein producing a ratio autofluorescence image comprises using ratiometric formula 1/(F440*F320); 1/F440; F340/(F340+F440); 1/(F440red+F440); F280*F340/F440, or F340/F440.

12. The method of claim 1, further comprising autoscaling or histogram equalizing the ratio reflectance image or the ratio autofluorescence image.

13. The method of claim 1, further comprising diagnosing a disease state based on the ratio reflectance image or the ratio autofluorescence image.

14. The method of claim 13, further comprising administering an agent to treat, prevent or ameliorate the disease state.

15. The method of claim 1, wherein the specimen is a tissue specimen or a sample of cells.

16. The method of claim 1, wherein the excitation signals comprise optical radiation having wavelengths between 260 nm and 650 nm.

17. The method of claim 1, wherein the emitted autofluorescence and the reflectance are optical radiation in a wavelength range of 340 nm to 650 nm.

18. The method of claim 1, wherein the specimen comprises a colon specimen.

19. The method of claim 1, wherein the specimen comprises a neoplastic colon specimen.

20. The method of claim 1, wherein the specimen comprises a colon adenocarcinoma specimen.

21. The method of claim 1, wherein the specimen comprises a polyploid colon specimen.

* * * * *